US007618979B2

(12) United States Patent
Leblanc et al.

(10) Patent No.: US 7,618,979 B2
(45) Date of Patent: Nov. 17, 2009

(54) PYRIDOPYRROLIZINE AND PYRIDOINDOLIZINE DERIVATIVES

(75) Inventors: Yves Leblanc, Kirkland (CA); Claude Dufresne, Dollard-des-Ormeaux (CA); Patrick Roy, Dollard-des-Ormeaux (CA)

(73) Assignee: Merck Frosst Canada Ltd., Kirkland, Quebec (CA)

( * ) Notice: Subject to any disclaimer, the term of this patent is extended or adjusted under 35 U.S.C. 154(b) by 598 days.

(21) Appl. No.: 10/532,633

(22) PCT Filed: Oct. 28, 2003

(86) PCT No.: PCT/CA03/01658

§ 371 (c)(1),
(2), (4) Date: Apr. 25, 2005

(87) PCT Pub. No.: WO2004/039807

PCT Pub. Date: May 13, 2004

(65) Prior Publication Data

US 2005/0272756 A1    Dec. 8, 2005

Related U.S. Application Data

(60) Provisional application No. 60/422,443, filed on Oct. 30, 2002, provisional application No. 60/482,626, filed on Jun. 26, 2003.

(51) Int. Cl.
*C07D 457/10* (2006.01)
*A61K 31/437* (2006.01)
(52) U.S. Cl. .......................................... 514/290; 546/80
(58) Field of Classification Search .................. 546/80; 514/290
See application file for complete search history.

(56) References Cited

U.S. PATENT DOCUMENTS

| 4,808,608 A | 2/1989 | Guindon et al. |
| 5,128,364 A | 7/1992 | Girard et al. |

FOREIGN PATENT DOCUMENTS

| EP | 0 166 591 A2 | 6/1985 |
| EP | 0 441 517 A2 | 1/1991 |
| WO | WO 98/25919 | 6/1998 |
| WO | WO 99/62555 | 12/1999 |
| WO | WO 02/94830 | 11/2002 |

OTHER PUBLICATIONS

Dorwald F. A. Side Reactions in Organic Synthesis, 2005, Wiley.*

* cited by examiner

*Primary Examiner*—Rita J Desai
(74) *Attorney, Agent, or Firm*—Dianne Brown; Mark R. Daniel

(57) ABSTRACT

Pyridopyrrolizine and pyridoindolizine derivatives are prostaglandin receptor antagonists useful for the treatment of prostaglandin-mediated diseases such as allergic rhinitis, nasal congestion and asthma.

16 Claims, No Drawings

PYRIDOPYRROLIZINE AND PYRIDOINDOLIZINE DERIVATIVES

CROSS REFERENCE TO RELATED APPLICATIONS

This application is the National Stage of International Application No. PCT/CA2003/001658, filed 28 Oct. 2003 which claims the benefit under 35 U.S.C. 119(e) of U.S. Provisional Application No. 60/422,443, filed 30 Oct. 2002, and U.S. Provisional Application No. 60/482,626, filed 26 Jun. 2003.

BACKGROUND OF THE INVENTION

The present invention relates to compounds and methods for treating prostaglandin mediated diseases, and certain pharmaceutical compositions thereof. More particularly, the compounds of the invention are structurally different from steroids, antihistamines or adrenergic agonists, and are antagonists of the nasal and pulmonary congestion effects of D-type prostaglandins.

Two review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137-154 and Journal of Lipid Mediators and Cell Signalling, 1996, 14, 83-87. An article from T. Tsuri et al. published in 1997 in Journal of Medicinal Chemistry, vol 40, pp. 3504-3507 states that "PGD2 is considered to be an important mediator in various allergic diseases such allergic rhinitis, atopic asthma, allergic conjunctivitis and atopic dermatitis." More recently, an article by Matsuoka et al. in *Science* (2000), 287:2013-7, describes PGD2 as being a key mediator in allergic asthma. In addition, patents such as U.S. Pat. No. 4,808,608 refer to prostaglandin antagonists as useful in the treatment of allergic diseases, and explicitly allergic asthma. PGD2 antagonists are described in, for example, European Patent Application 837,052 and PCT Application WO98/25919, as well as WO99/62555.

SUMMARY OF THE INVENTION

The present invention provides novel compounds which are prostaglandin receptor antagonists; more particularly, they are prostaglandin D2 receptor (DP receptor) antagonists. Compounds of the present invention are useful for the treatment of various prostaglandin-mediated diseases and disorders; accordingly the present invention provides a method for the treatment of prostaglandin-mediated diseases using the novel compounds described herein, as well as pharmaceutical compositions containing them.

DETAILED DESCRIPTION OF THE INVENTION

The present invention relates to compounds of formula I:

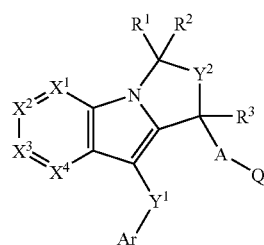

and pharmaceutically acceptable salts and hydrates thereof, wherein:

A is selected from $C_{1-3}$alkyl optionally substituted with one to four halogen atoms, $O(CH_2)_{1-2}$, and $S(CH_2)_{1-2}$;

Ar is aryl or heteroaryl each optionally substituted with one to four groups independently selected from $R^g$;

Q is selected from:
(1) COOH,
(2) $CONR^aR^b$,
(3) $C(O)NHSO_2R^c$,
(4) $SO_2NHR^a$,
(5) $SO_3H$,
(6) $PO_3H_2$, and
(7) tetrazolyl;

one of $X^1$, $X^2$, $X^3$ or $X^4$ is nitrogen and the others are independently selected from CH and C—$R^g$;

$Y^1$ is selected from —$(CR^dR^e)_a$—X—$(CR^dR^e)_b$—, phenylene, $C_{3-6}$cycloalkylidene and $C_{3-6}$cycloalkylene, wherein a and b are integers 0-1 such that the sum of a and b equals 0, 1 or 2, and X is a bond, O, S, $NR^a$, C(O), $CH(OR^a)$, OC(O), C(O)O, C(O)$NR^a$, OC(O)$NR^a$, $NR^a$C(O), $CR^d$=$CR^e$ or C≡C;

$Y^2$ is selected from $(CR^dR^e)_m$ and $CR^d$=$CR^e$;

$R^1$ is selected from H, CN, $OR^a$, $S(O)_nC_{1-6}$alkyl and $C_{1-6}$alkyl optionally substituted with one to six groups independently selected from halogen, $OR^a$ and $S(O)_nC_{1-6}$alkyl;

$R^2$ is selected from H and $C_{1-6}$alkyl optionally substituted with one to six halogen; or $R^1$ and $R^2$ together represent an oxo; or $R^1$ and $R^2$ taken together form a 3- or 4-membered ring containing 0 or 1 heteroatom selected from $NR^f$, S, and O optionally substituted with one or two groups selected from F, $CF_3$ and $CH_3$;

$R^3$ is selected from H and $C_{1-6}$alkyl optionally substituted with one to six groups independently selected from $OR^a$ and halogen;

$R^a$ and $R^b$ are independently selected from H, $C_{1-10}$alkyl, $C_{2-10}$alkenyl, $C_{2-10}$alkynyl, Cy and Cy $C_{1-10}$alkyl, wherein said alkyl, alkenyl, alkynyl and Cy are optionally substituted with one to six substituents independently selected from halogen, amino, carboxy, $C_{1-4}$alkyl, $C_{1-4}$alkoxy, aryl, heteroaryl, aryl $C_{1-4}$alkyl, hydroxy, $CF_3$, $OC(O)C_{1-4}$alkyl, $OC(O)NR^iR^j$, and aryloxy; or $R^a$ and $R^b$ together with the atom(s) to which they are attached form a heterocyclic ring of 4 to 7 members containing 0-2 additional heteroatoms independently selected from oxygen, sulfur and N—$R^f$;

$R^c$ is selected from $C_{1-6}$alkyl optionally substituted with one to six halogen, aryl and heteroaryl, wherein said aryl and heteroaryl are optionally substituted with one to three groups selected from halogen, $OC_{1-6}$alkyl, O-halo$C_{1-6}$alkyl, $C_{1-6}$alkyl and halo$C_{1-6}$alkyl;

$R^d$ and $R^e$ are independently H, halogen, aryl, heteroaryl, $C_{1-6}$alkyl or halo$C_{1-6}$alkyl;

$R^f$ is selected from H, $C_{1-6}$alkyl, halo$C_{1-6}$alkyl, Cy, $C(O)C_{1-6}$alkyl, $C(O)$halo$C_{1-6}$ alkyl, and C(O)—Cy;

$R^g$ is selected from
(1) halogen,
(2) CN,
(3) $C_{1-6}$alkyl optionally substituted with one to eight groups independently selected from aryl, heteroaryl, halogen, $NR^aR^b$, $C(O)R^a$, $C(OR^a)R^aR^b$, $SR^a$ and $OR^a$, wherein aryl, heteroaryl and alkyl are each optionally substituted with one to six groups independently selected from halogen, $CF_3$, and COOH, (4) $C_{2-6}$alkenyl optionally substituted with one to six groups independently selected from halogen and $OR^a$,
(5) Cy
(6) $C(O)R^a$,
(7) $C(O)OR^a$,
(8) $CONR^aR^b$,
(9) $OCONR^aR^b$,
(10) $OC_{1-6}$alkyl, wherein alkyl is optionally substituted with one to six substituents selected from halogen, aryl, heteroaryl, OH and $OC(O)R^a$,
(11) O—Cy,
(12) $S(O)_nC_{1-6}$alkyl, wherein alkyl is optionally substituted with one to six substituents selected from halogen, aryl, heteroaryl, OH, and $OC(O)R^a$,
(13) $S(O)_n$—Cy,
(14) —$NR^aS(O)_nR^b$,
(15) —$NR^aR^b$,
(16) —$NR^aC(O)R^b$,
(17) —$NR^aC(O)OR^b$,
(18) —$NR^aC(O)NR^aR^b$,
(19) $S(O)_nNR^aR^b$,
(20) $NO_2$,
(21) $C_{5-8}$cycloalkenyl, wherein Cy is optionally substituted with one to eight groups independently selected from halogen, $C(O)R^a$, $OR^a$, $C_{1-3}$alkyl, aryl, heteroaryl and $CF_3$;

$R^i$ and $R^j$ are independently selected from hydrogen, $C_{1-10}$alkyl, Cy and Cy—$C_{1-10}$alkyl; or $R^i$ and $R^j$ together with the nitrogen atom to which they are attached form a ring of 5 to 7 members containing 0-2 additional heteroatoms independently selected from oxygen, sulfur and N—$R^f$;

Cy is selected from heterocyclyl, aryl, and heteroaryl;

m is 1, 2 or 3; and n is 0, 1 or 2.

The invention also encompasses pharmaceutical compositions containing a compound of formula I, and methods for treatment or prevention of prostaglandin mediated diseases using compounds of formula I.

The invention is described using the following definitions unless otherwise indicated.

The term "halogen" or "halo" includes F, Cl, Br, and I.

The term "alkyl" refers to linear, branched and cyclic and bicyclic structures and combinations thereof, containing the indicated number of atoms. Non-limiting examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclobutyl, cyclopentyl, cyclohexyl, cycloheptyl, cyclopropylmethyl, cyclopentylethyl, methyl substituted cyclopropyl, ethyl substituted cyclobutyl, adamantyl, cyclododecylmethyl, 2-ethyl-1-bicyclo[4.4.0]decyl and the like. For example, the term $C_{1-6}$alkyl encompasses acyclic alkyl groups having the indicated number of carbon atoms as well as —$C_x$alkyl-$C_z$cycloalkyl wherein x is 0 to 3 and z is 3 to 6 with the proviso that x+z=3 to 6.

"Cycloalkylidene" refers to the following bivalent radical where the points of attachement are on the same carbon atom:

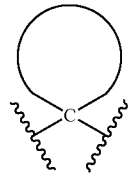

"Cycloalkylene" refers to the following bivalent radical where the points of attachment are on different carbon atoms:

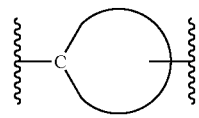

"Phenylene" refers to the following bivalent radical and includes 1,2-phenylene, 1,3-phenylene and 1,4-phenylene:

"Haloalkyl" means an alkyl group as described above wherein one or more hydrogen atoms have been replaced by halogen atoms, with up to complete substitution of all hydrogen atoms with halo groups. $C_{1-6}$haloalkyl, for example, includes —$CF_3$, —$CH_2CF_3$, —$CF_2CF_3$ and the like.

"Alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

"Haloalkoxy" means an alkoxy group as described above in which one or more hydrogen atoms have been replaced by halogen atoms, with up to complete substitution of all hydrogen atoms with halo groups. $C_{1-6}$haloalkoxy, for example, includes —$OCF_3$, —$OCH_2CF_3$, —$OCF_2CF_3$ and the like.

"Alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

"Heterocyclyl" refers to a non-aromatic ring having 1 to 4 heteroatoms said ring being isolated or fused to a second ring selected from 3- to 7-membered alicyclic ring containing 0 to 4 heteroatoms, aryl and heteroaryl, wherein said heteroatoms are independently selected from O, N and S. Non-limiting examples of heterocyclyl include oxetanyl, 1,3-dithiacyclopentane, dihydrobenzofuran, and the like.

"Aryl" means a 6-14 membered carbocyclic aromatic ring system comprising 1-3 benzene rings. If two or more aromatic rings are present, then the rings are fused together, so that adjacent rings share a common bond. Examples include phenyl and naphthyl.

The term "heteroaryl" (Het) as used herein represents a 5-10 membered aromatic ring system containing one ring or two fused rings, 1-4 heteroatoms, selected from O, S and N. Het includes, but is not limited to, tetrazolyl, benzothienyl, quinolinyl, benzothiazolyl, furanyl, pyrimidinyl, purinyl, naphthyridinyl, imidazolyl, isoxazolyl, isothiazolyl, oxadiazolyl, oxazolyl, pyrazolyl, pyridyl, pyrrolyl, tetrazinyl, thiazolyl, thiadiazolyl, thienyl, triazinyl, triazolyl, 1H-pyrrole-2,5-dionyl, 2-pyrone, 4-pyrone, pyrrolopyridine, furopyridine and thienopyridine.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "prophylaxis" means preventing or delaying the onset or the progression of a disease or disorder, or the signs and symptoms associated with such disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, and pharmaceutically acceptable excipients.

For compounds of formula I, examples of A include, but are not limited to, $CH_2$, $CH_2CH_2$, $CH_2CH(CH3)$, $CH(Cl)$, $CH_2CF_2CH_2$, $CH(Cl)CH_2CH(F)$, $OCH_2$, $OCH_2CH_2$, $SCH_2$ and $SCH_2CH_2$. Examples of Q include, but are not limited to, $CO_2H$, $CONH_2$, $CONHCH_3$, $CONHPh$, $CON(CH_3)_2$, $CON(CH_2)_4$, $CONHSO_2CH_3$, $SO_2NHPh$, tetrazolyl and the like.

Examples of $Y^1$ include, but are not limited to, $CH_2$, $CH_2CH_2$, $CH_2CH(CH3)$, $CH(Cl)$, $CH(Ph)$, $CH_2CH(CF_3)$, $CF_2CH_2$, $CH(Cl)CH_2CH(F)$, $OCH_2$, $OCH_2CH_2$, $SCH_2$, $CH_2SCH_2$, S, O, C(O), $CH_2C(O)$, $CH_2C(O)O$, $CH_2C(O)OCH_2$, NH, NHC(O), $CH_2NHC(O)$, $CH_2NHC(O)CH_2$, CH=CH, $CH_2CH=CHCH_2$, $CH_2C≡C$, 1,4-phenylene, 1,1-cyclopropylidene, 1,3-cyclohexylene, and the like.

Examples of Ar include, but are not limited to, phenyl, 2-, 3-, 4-chlorophenyl, 2-, 3-, 4-bromophenyl, 2-, 3-, 4-fluorophenyl, 3,4-diclorophenyl, 2,3-dichlorophenyl, 2,4-dichlorophenyl, 2,5-dichlorophenyl, 2,6-dichlorophenyl, 3,5-dichlorophenyl, 3-chloro-4-fluorophenyl, 2-chloro-4-fluorophenyl, 4-chloro-2-fluorophenyl, 2-cyanophenyl, 4-methylphenyl, 4-isopropylphenyl, 4-trifluoromethylphenyl, biphenyl, naphthyl, 3-methoxyphenyl, 3-carboxyphenyl, 2-carboxamidophenyl, 4-methoxyphenyl, 3-phenoxyphenyl, 4-(4-pyridyl)phenyl, 4-methylsulfonylphenyl, 3-dimethylaminophenyl, 5-tetrazolyl, 1-methyl-5-tetrazolyl, 2-methyl-5-tetrazolyl, 2-benzothienyl, 2-benzofuranyl, 2-indolyl, 2-quinolinyl, 7-quinolinyl, 2-benzothiazolyl, 2-benzimidazolyl, 1-benzotriazolyl, 2-furanyl, 3-furanyl, 2-imidazolyl, 5-imidazolyl, 5-isoxazolyl, 4-isoxazolyl, 4-isothiazolyl, 1,2,4-oxadiazol-5-yl, 2-oxazolyl, 4-oxazolyl, 4-pyrazolyl, 5-pyrazolyl, 2-pyridyl, 3-pyridyl, 2-pyrazinyl, 5-pyrimidinyl, 2-pyrrolyl, 4-thiazolyl, 1,2,4-thiadiazol-3-yl, 1,2,5-thiadiazol-4-yl, 1,2,3-thiadiazol-4-yl, 1,2,5-oxadiazol-4-yl, 1,2,3-oxadiazol-4-yl, 1,2,4-triazol-5-yl, 1,2,3-triazol-4-yl, 3-thienyl, 1,2,4-triazol-5-yl, pyrrolo-pyridine, furo[3,2-b]pyridin-2-yl, thieno[2,3-b]pyridin2-yl, 5(H)-2-oxo-4-furanyl, 5(H)-2-oxo-5-furanyl, (1H,4H)-5-oxo-1,2,4-triazol-3-yl, 4-oxo-2-benzopyranyl, and the like.

Examples of $Y^2$ include, but are not limited to, $CH_2$, $CH_2CH_2$, $CH_2CH_2CH_2$, $CH(Cl)$, $CCl_2$, $CH(CF_3)$, $CH(Ph)$, $CH_2CHCl$, $C(Cl)=CH_2$, $C(Cl)=C(Cl)$, CH=CH, CH=C(CF_3)$, and the like.

Examples of $X^1$, $X^2$, $X^3$ and $X^4$ include, but are not limited to, N, CH, C—$CH_3$, C—$CH(CH_3)_2$, C-Ph, C—Cl, C—Br, C—F, C—$CF_3$, C—$C(O)CH_3$, C—$C(O)OH$, C—$C(O)NH_2$, C—$C(O)N(CH_2)_2O(CH_2)_2$, C—$OCH_3$, C—$OCF_3$, C—OPh, C—$SCH_3$, C—$SOCH_3$, C—$SO_2CH_3$, C—$SO_2Ph$, C—$NH_2$, C—$N(CH_3)_2$, C—$N(CH_3)C(O)CH_3$, C—$N(CH_3)C(O)OCH_3$, C—$NHC(O)NHCH_3$, C-cyclopropyl, C-cyclobutyl, C-cyclopentyl, and the like.

Examples of $R^1$ include, but are not limited to, hydrogen, cyano, $CH_3$, $CH_2CH_3$, $CF_3$, $CH_2CH_2Cl$, cyclopropyl, and the like.

Examples of $R^2$ include, but are not limited to, hydrogen, $CH_3$, $CH_2CH_3$, $CF_3$, $CH_2CH_2Cl$, cyclopropyl, and the like.

Examples of $R^3$ include, but are not limited to, hydrogen, $CH_3$, $CH_2CH_3$, $CF_3$, $CH_2CH_2Cl$, $CH_2CH_2OH$, cyclopropyl, and the like.

In one embodiment of formula I, the moiety A-Q is $CH_2CO_2H$.

In a second embodiment of formula I are compounds wherein the moiety $Y^1$—Ar is S-aryl or C(O)-aryl, wherein said aryl is naphthyl or phenyl optionally substituted with 1 to 2 groups selected from $R^g$. In one subset thereof, $Y^1$—AR is S-phenyl optionally substituted with 1 or 2 groups selected from halogen, $C_{1-6}$ alkyl and trifluoromethyl.

In a third embodiment of formula I are compounds wherein $X^1$ is nitrogen and $X^2$, $X^3$ and $X^4$ are independently selected from CH and $CR^g$. In one subset, one of $X^2$, $X^3$ and $X^4$ is $CR^g$, and the others are CH. In another subset one of $X^2$, $X^3$ and $X^4$ is CH, and the others are $CR^g$.

In a fourth embodiment of formula I are compounds wherein $X^3$ is nitrogen and $X^1$, $X^2$ and $X^4$ are independently selected from CH and $CR^g$. In one subset, one of $X^1$, $X^2$ and $X^4$ is $CR^g$, and the others are CH. In another subset one of $X^1$, $X^2$ and $X^4$ is CH, and the others are $CR^g$.

In fifth embodiment of formula I are compounds wherein one of $X^1$, $X^2$ or $X^3$ is nitrogen and the others are CH or $CR^g$, and $X^4$ is $CR^g$. In one subset, one of $X^1$, $X^2$ or $X^3$ is nitrogen and the others are CH or C—$C_{1-6}$alkyl, and $X^4$ is C—$S(O)_n$—$C_{1-6}$alkyl or C—$C_{1-6}$alkyl optionally substituted with $OR^a$.

In sixth embodiment of formula I are compounds wherein $Y^2$ is selected from $CH_2$ and $CH_2CH_2$.

In seventh embodiment of formula I are compounds where $R^1$, $R^2$ and $R^3$ are each hydrogen, or $R^1$ and $R^2$ together is oxo, and $R^3$ is hydrogen.

One group of compounds within formula I is represented by the formula Ia:

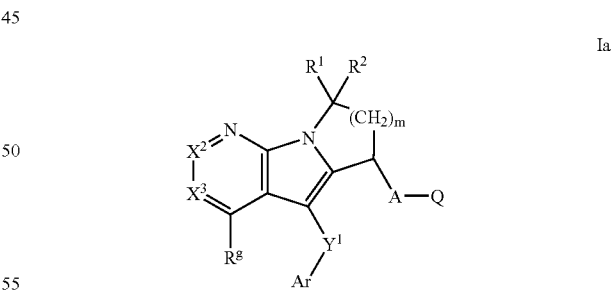

Ia wherein $X^2$ and $X^3$ are independently CH or C—$R^g$, A, Ar, Q, $Y^1$, $R^1$, $R^2$, m and $R^g$ are as defined under formula I. In one embodiment of formula Ia are compounds wherein $X^2$ and $X^3$ are each CH. In another embodiment are compounds wherein $R^1$ and $R^2$ are each H. In yet another embodiment, A-Q is $CH_2CO_2H$. In yet another embodiment $Y^1$—Ar is S-phenyl optionally substituted with 1 or 2 groups independently selected from halogen, $C_{1-6}$ alkyl and trifluoromethyl. In yet another embodiment, $R^g$ is selected from $SO_2$—$C_{1-6}$alkyl and $C_{1-6}$alkyl.

Another group of compounds within formula I is represented by the formula Ib:

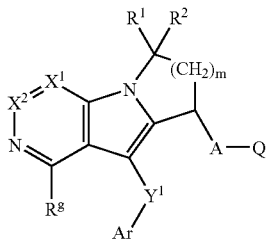

wherein $X^1$ and $X^2$ are independently CH or C—$R^g$, A, Ar, Q, $Y^1$, $R^1$, $R^2$, m and $R^g$ are as defined under formula I. In one embodiment of formula Ia are compounds wherein $X^1$ and $X^2$ are each CH. In another embodiment are compounds wherein $R^1$ and $R^2$ are each H. In yet another embodiment, A-Q is $CH_2CO_2H$. In yet another embodiment $Y^1$—Ar is S-phenyl optionally substituted with 1 or 2 groups independently selected from halogen, $C_{1-6}$ alkyl and trifluoromethyl. In yet another embodiment, $R^g$ is selected from $SO_2$—$C_{1-6}$alkyl and $C_{1-6}$alkyl.

Another group of compounds within formula I is represented by the formula Ic:

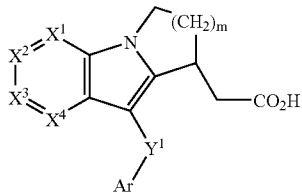

wherein one of $X^1$, $X^2$ and $X^3$ is N and the others are each CH, $X^4$ is $CR^g$, m is 1 or 2, and Ar, $Y^1$ and m are as defined under formula I. In one embodiment, Ar is phenyl optionally substituted with 1 or 2 groups independently selected from halogen, $C_{1-3}$alkyl and trifluoromethyl. In another embodiment $Y^1$ is S or C(O). In yet another embodiment, $X^4$ is selected from C—S(O)$_n$—$C_{1-6}$alkyl and C—$C_{1-6}$alkyl optionally substituted with $OR^a$.

Representative compounds of formula I are shown in the following Tables:

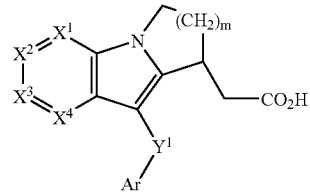

| $X^1$ | $X^2$ | $X^3$ | $X^4$ | Ar | $Y^1$ | m |
|---|---|---|---|---|---|---|
| N | CH | CH | C(SO$_2$CH$_3$) | 4-Cl—Ph | S | 2 |
| N | CH | CH | C(SCH3) | 4-Cl—Ph | S | 2 |
| N | CH | CH | C(SO$_2$CH$_3$) | 3,4-diCl—Ph | S | 2 |
| N | CH | CH | C(SO$_2$CH$_3$) | 4-Cl—Ph | C(O) | 2 |
| N | CH | CH | C(SO$_2$CH$_3$) | 4-Br—Ph | S | 2 |
| CH | CH | N | C(SO$_2$CH$_3$) | 3,4-diCl—Ph | S | 1 |
| CH | CH | N | C(SO$_2$CH$_3$) | 3,4-diCl—Ph | S | 2 |
| N | CH | CH | C(SO$_2$CH$_3$) | 4-CF$_3$—Ph | S | 2 |

-continued

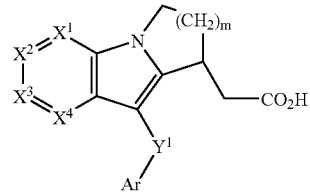

| $X^1$ | $X^2$ | $X^3$ | $X^4$ | Ar | $Y^1$ | m |
|---|---|---|---|---|---|---|
| N | CH | CH | C(SO$_2$CH$_3$) | 2-Cl-4-F—Ph | S | 2 |
| N | CH | CH | C(SO$_2$CH$_3$) | 2-naphthyl | S | 2 |
| N | CH | CH | C(SO$_2$CH$_3$) | 2,3-diCl—Ph | S | 2 |
| N | CH | CH | C(SO$_2$CH$_3$) | 4-CH$_3$—Ph | S | 2 |
| N | CH | CH | C(SO$_2$CH$_3$) | Ph | S | 2 |
| N | CH | CH | C(SO$_2$CH$_3$) | 2,4-diCl—Ph | S | 2 |
| CH | N | CH | C(SO$_2$CH$_3$) | 4-Cl—Ph | S | 2 |
| CH | CH | N | C(SO$_2$CH$_3$) | 4-Cl—Ph | S | 2 |
| N | C(CH3) | CH | C(SO$_2$CH$_3$) | 4-Cl—Ph | S | 2 |
| N | CH | C(CH3) | C(SO$_2$CH$_3$) | 4-Cl—Ph | S | 2 |
| CH | C(CH3) | N | C(SO$_2$CH$_3$) | 4-Cl—Ph | S | 2 |
| C(CH3) | CH | N | C(SO$_2$CH$_3$) | 4-Cl—Ph | S | 2 |
| N | CH | CH | C(CH(CH$_3$)$_2$) | 4-F—Ph | S | 2 |
| N | CH | CH | C(CH(CH$_3$)$_2$) | 4-Cl—Ph | S | 2 |
| N | CH | CH | C(CH(CH$_3$)$_2$) | 2,4-diCl—Ph | S | 2 |
| N | CH | CH | C(CH(CH$_3$)$_2$) | 4-Br—Ph | S | 2 |
| N | CH | CH | C(CH(CH$_3$)$_2$) | 2-Cl-4-F—Ph | S | 2 |
| N | CH | CH | C(CH(CH$_3$)$_2$) | 3,4-diCl—Ph | S | 2 |
| CH | CH | N | C(CH(CH$_3$)$_2$) | 4-F—Ph | S | 2 |
| CH | CH | N | C(CH(CH$_3$)$_2$) | 4-Cl—Ph | S | 2 |
| CH | CH | N | C(CH(CH$_3$)$_2$) | 2,4-diCl—Ph | S | 2 |
| CH | CH | N | C(CH(CH$_3$)$_2$) | 4-Br—Ph | S | 2 |
| CH | CH | N | C(CH(CH$_3$)$_2$) | 2-Cl-4-F—Ph | S | 2 |
| CH | CH | N | C(CH(CH$_3$)$_2$) | 3,4-diCl—Ph | S | 2 |
| CH | CH | N | C(CH(CH$_3$)$_2$) | 4-F—Ph | S | 1 |
| CH | CH | N | C(CH(CH$_3$)$_2$) | 4-Cl—Ph | S | 1 |
| CH | CH | N | C(CH(CH$_3$)$_2$) | 2,4-diCl—Ph | S | 1 |
| CH | CH | N | C(CH(CH$_3$)$_2$) | 4-Br—Ph | S | 1 |
| CH | CH | N | C(CH(CH$_3$)$_2$) | 2-Cl-4-F—Ph | S | 1 |
| CH | CH | N | C(CH(CH$_3$)$_2$) | 3,4-diCl—Ph | S | 1 |
| CH | N | CH | C(CH(CH$_3$)$_2$) | 4-F—Ph | S | 1 |
| CH | N | CH | C(CH(CH$_3$)$_2$) | 4-Cl—Ph | S | 1 |
| CH | N | CH | C(CH(CH$_3$)$_2$) | 2,4-diCl—Ph | S | 1 |
| CH | N | CH | C(CH(CH$_3$)$_2$) | 4-Br—Ph | S | 1 |
| CH | N | CH | C(CH(CH$_3$)$_2$) | 2-Cl-4-F—Ph | S | 1 |
| CH | N | CH | C(CH(CH$_3$)$_2$) | 3,4-diCl—Ph | S | 1 |
| CH | N | CH | C(CH(CH$_3$)$_2$) | 4-F—Ph | S | 2 |
| CH | N | CH | C(CH(CH$_3$)$_2$) | 4-Cl—Ph | S | 2 |
| CH | N | CH | C(CH(CH$_3$)$_2$) | 2,4-diCl—Ph | S | 2 |
| CH | N | CH | C(CH(CH$_3$)$_2$) | 4-Br—Ph | S | 2 |
| CH | N | CH | C(CH(CH$_3$)$_2$) | 2-Cl-4-F—Ph | S | 2 |
| CH | N | CH | C(CH(CH$_3$)$_2$) | 3,4-diCl—Ph | S | 2 |
| N | CH | CH | C(CH(OCH$_3$)(CH$_2$CH$_3$)) | 4-Cl—Ph | S | 2 |
| N | CH | CH | C(CH(OCH$_3$)(CH$_2$CH$_3$)) | 4-Cl—Ph | S | 1 |
| CH | N | CH | C(CH(OCH$_3$)(CH$_2$CH$_3$)) | 4-Cl—Ph | S | 1 |
| CH | N | CH | C(CH(OCH$_3$)(CH$_2$CH$_3$)) | 4-Cl—Ph | S | 2 |
| CH | CH | N | C(CH(OCH$_3$)(CH$_2$CH$_3$)) | 4-Cl—Ph | S | 2 |
| CH | CH | N | C(CH(OCH$_3$)(CH$_2$CH$_3$)) | 4-Cl—Ph | S | 1 |
| N | CH | CH | C(C(CH$_3$)$_3$) | 4-Cl—Ph | S | 2 |
| N | CH | CH | C(C(CH$_3$)$_3$) | 3,4-diCl—Ph | S | 2 |
| N | CH | CH | C(C(CH$_3$)$_3$) | 4-Br—Ph | S | 2 |
| N | CH | CH | C(C(CH$_3$)$_3$) | 4-CF$_3$—Ph | S | 2 |
| N | CH | CH | C(C(CH$_3$)$_3$) | 2-Cl-4-F—Ph | S | 2 |
| N | CH | CH | C(C(CH$_3$)$_3$) | 2-naphthyl | S | 2 |
| N | CH | CH | C(C(CH$_3$)$_3$) | 2,3-diCl—Ph | S | 2 |
| N | CH | CH | C(C(CH$_3$)$_3$) | 4-CH$_3$—Ph | S | 2 |
| N | CH | CH | C(C(CH$_3$)$_3$) | Ph | S | 2 |
| N | CH | CH | C(C(CH$_3$)$_3$) | 2,4-diCl—Ph | S | 2 |

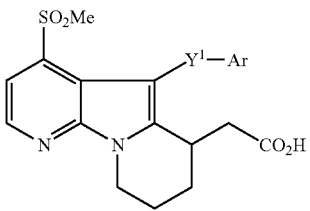

| Ar | Y¹ |
|---|---|
| 5-tetrazolyl | S |
| 2-pyrrolyl | S |
| 1,2,4-triazoly-3-yl | S |
| 1,2,3-triazol-4-yl | S |
| 5-imidazolyl | S |
| 4-pyrazolyl | S |
| 5-pyrazolyl | S |
| (1H,4H)-5-oxo-1,2,4-triazol-3-yl | S |
| 4-isothiazolyl | S |
| 1,2,5-thiadiazol-5-yl | S |
| 1,2,5-oxadiazol-5-yl | S |
| 3-furanyl | S |
| 1,2,3-thiadiazol-4-yl | S |
| 1,2,3-oxadiazol-4-yl | S |
| 4-isoxazolyl | S |
| 3-thienyl | S |
| 4-oxazolyl | S |
| 4-thiazolyl | S |
| (5H)-2-oxo-5-furanyl | S |
| (5H)-2-oxo-4-furanyl | S |
| 1,2,4-oxadiazol-5-yl | S |
| 3-pyridyl | S |
| 2-pyrazinyl | S |
| 5-pyrimidinyl | S |
| 2-indolyl | S |
| 2-benzothienyl | S |
| 2-benzofuranyl | S |
| 4-oxo-benzopyran-2-yl | S |
| 2-quinolinyl | S |
| 2-benzimidazolyl | S |
| 2-benzoxazolyl | S |
| 2-benzothiazolyl | S |
| 1-benzotriazolyl | CH₂S |
| thieno[2,3-b]pyridin-2-yl | S |

For purposes of this specification, the following abbreviations have the indicated meanings:
Ac=acetyl
AcO=acetate
BOC=t-butyloxycarbonyl
CBZ=carbobenzoxy
CDI=carbonyldiimidazole
DCC=1,3-dicyclohexylcarbodiimide
DCE=1,2-dichloroethane
DIBAL=diisobutyl aluminum hydride
DIEA=N,N-diisoproylethylamine
DMAP=4-(dimethylamino)pyridine
DMF=dimethylformamide
EDCI=1-(3-dimethylaminopropyl)-3-ethylcarbodiimide hydrochloride
EDTA=ethylenediaminetetraacetic acid, tetrasodium salt hydrate
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOBt=1-hydroxybenzotriazole
HRMS=high resolution mass spectrometry
ICBF=isobutyl chloroformate
KHMDS=potassium hexamethyldisilazane
LDA=lithium diisopropylamide
MCPBA=metachloroperbenzoic acid
MMPP=magnesium monoperoxyphthlate hexahydrate
Ms=methanesulfonyl=mesyl
MsO=methanefulfonate=mesylate
NBS=N-bromosuccinimide
NMM=4-methylmorpholine
NMP=N-methylpyrrolidinone
PCC=pyridinium chlorochromate
PDC=pyridinium dichromate
Ph=phenyl
PPTS=pyridinium p-toluene sulfonate
pTSA=p-toluene sulfonic acid
PyH.Br₃=pyridine hydrobromide perbromide
r.t./RT=room temperature
rac.=racemic
TFA=trifluoroacetic acid
TfO=trifluoromethanesulfonate=triflate
THF=tetrahydrofuran
TLC=thin layer chromatography
TMSCI=trimethylsilyl chloride Alkyl Group Abbreviations
Me=methyl
Et=ethyl
n-Pr=normal propyl
i-Pr=isopropyl
c-Pr=cyclopropyl
n-Bu=normal butyl
i-Bu=isobutyl
c-Bu=cyclobutyl
s-Bu=secondary butyl
t-Bu=tertiary butyl Optical Isomers—Diastereomers—Tautomers Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid or base as a resolving agent, or by chiral separation techniques such as separation by HPLC using a chiral column.

Alternatively, any enantiomer of a compound of the general formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethyl amine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I are meant to also include the pharmaceutically acceptable salts.

Utilities

Compounds of formula I are antagonists of prostaglandin D2. The ability of compounds of formula I to interact with prostaglandin D2 receptor makes them useful for preventing or reversing undesirable symptoms caused by prostaglandins in a mammalian, especially human subject. The antagonism of the actions of prostaglandin D2 indicates that the compounds and pharmaceutical compositions thereof are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastic tumor growth and hence can be used in the treatment of cancer. Compounds of formula I may also be of use in the treatment and/or prevention prostaglandin D2 mediated proliferation disorders such as may occur in diabetic retinopathy and tumor angiogenesis. Compounds of formula I may also inhibit prostanoid-induced smooth muscle contraction by antagonizing contractile prostanoids or mimicking relaxing prostanoids and hence may be use in the treatment of dysmenorrhea, premature labor and eosinophil related disorders.

Accordingly, another aspect of the invention provides a method of treating or preventing a prostaglandin D2 mediated disease comprising administering to a mammalian patient in need of such treatment a compound of formula I in an amount which is effective for treating or preventing said prostaglandin D2 mediated disease. Prostaglandin D2 mediated diseases include, but are not limited to, allergic rhinitis, nasal congestion, rhinorrhea, perennial rhinitis, nasal inflammation, asthma including allergic asthma, chronic obstructive pulmonary diseases and other forms of lung inflammation; pulmonary hypotension; sleep disorders and sleep-wake cycle disorders; prostanoid-induced smooth muscle contraction associated with dysmenorrhea and premature labor; eosinophil related disorders; thrombosis; glaucoma and vision disorders; occlusive vascular diseases, such as for example atherosclerosis; congestive heart failure; diseases or conditions requiring a treatment of anti-coagulation such as post-injury or post surgery treatment; rheumatoid arthritis and other inflammatory diseases; gangrene; Raynaud's disease; mucus secretion disorders including cytoprotection; pain and migraine; diseases requiring control of bone formation and resorption such as for example osteoporosis; shock; thermal regulation including fever; rejection in organ transplant and by-pass surgery, and immune disorders or conditions in which immunoregulation is desirable. More particularly the disease to be treated is one mediated by prostaglandin D2 such as nasal congestion, allergic rhinitis, pulmonary congestion, and asthma including allergic asthma.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg to 200 mg, or 400 mg.

Pharmaceutical Compositions

Another aspect of the present invention provides pharmaceutical compositions comprising a compound of formula I with a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above, Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of prostaglandin mediated diseases, compound of formula I may be co-administered with other therapeutic agents. Thus in another aspect the present invention provides pharmaceutical compositions for treating prostaglandin D2 mediated diseases comprising a therapeutically effective amount of a compound of formula I and one or more other therapeutic agents. Suitable therapeutic agents for combination therapy with a compound of formula I include: (1) a prostaglandin receptor antagonist; (2) a corticosteroid such as triamcinolone acetonide; (3) a β-agonist such as salmeterol, formoterol, terbutaline, metaproterenol, albuterol and the like; (4) a leukotriene modifier, such as a leukotriene antagonist or a lipooxygenase inhibitor such as montelukast, zafirlukast, pranlukast, or zileuton; (5) an antihistamine (histamnine H1 antagonist) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, norastemizole, terfenadine, loratadine, cetirizine, levocetirizine, fexofenadine, desloratadine, and the like; (6) a decongestant including phenylephrine, phenylpropanolamine, pseudophedrine, oxymetazoline, ephinephrine, naphazoline, xylometazoline, propylhexedrine, or levo-desoxyephedrine; (7) an antiitussive including codeine, hydrocodone, caramiphen, carbetapentane, or dextramethorphan; (8) another prostaglandin ligand including prostaglandin F agonist such as latanoprost; misoprostol, enprostil, rioprostil, ornoprostol or rosaprostol;

(9) a diuretic; (10) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenyicarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors such as celecoxib and rofecoxib, etoricoxib and valdecoxib; (12) inhibitors of phosphodiesterase type IV (PDE-IV) e.g. Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents such as muscarinic antagonists (ipratropium bromide and tiotropium bromide), as well as selective muscarinic M3 antagonists; (18) steroids such as beclorrsethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2 or BK1) antagonists, TP receptor antagonists such as seratrodast, neurokinin antagonists (NK1/NK2), VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206.

In addition, the invention encompasses a method of treating prostaglandin $D_2$ mediated diseases comprising: administering to a patient in need of such treatment a therapeutically effective amount of the compound of formula I, co-administered with one or more of such ingredients as listed immediately above. The amounts of active ingredients may be those commonly used for each active ingredient when it is administered alone, or in some instances the combination of active ingredients may result in lower dosage for one or more of the active ingredients.

Methods of Synthesis

Compounds of Formula I of the present invention may be prepared according to the synthetic routes outlined in Schemes A to F and by following the methods described in the Examples provided herein. Both the schemes and specific examples provided herein are for illustrative purpose, and a person skilled in the art will appreciate that other compounds of the present invention may be analogously prepared using the illustrative procedures, or they may be obtained from exemplified compounds via functional group interconversion procedures that are generally known in the art, or they may be prepared by other procedures that are known to persons skilled in the art of organic synthesis.

Method A

Pyridine 1 can be formylated to give aldehyde 2 according to the procedure described in *J. Heterocyclic Chem.*, p 81, (1988), *Heterocycles* p. 151, 1993 or in *Synthesis*, p. 306 (1999). Halogen displacement with sodium thiomethoxide or sodium methoxide, followed by condensation with methylazidoacetate provides azido olefin 4 which is cyclized under thermal conditions to give indole 5 (see for example, Tetrahedron Lett., 2000, 41:4777-4780). For the fused five-membered ring series, 5 is treated with methyl acrylate in the presence of KOtBu, followed by decarboxylation with HCl/EtOH to give 6 (m=1). For the fused six and seven-membered ring series, 5 is treated with NaH/DMF and the appropriate bromo ester, followed by cyclization with KOtBu/TBF and finally HCl/EtOH to effect decarboxylation to give 6 (m=2,3). The formation of ester 7 is carried out using Reformatsky conditions followed by deoxygenation with TMSCl/NaI, or via Horner-Emmonds reaction followed by hydrogenation over $PtO_2$ or $Pd(OH)_2$. Alternatively, 6 can be converted to 7 by reduction with $NABH_4$ in ethanol-THF followed by reaction with diphenyl chlorophosphate using NaHMDS as a base. The resulting phosphate is treated with dimethyl malonate and NaHMDS. The bis ester is heated in DMSO with NaCl to provide 7.

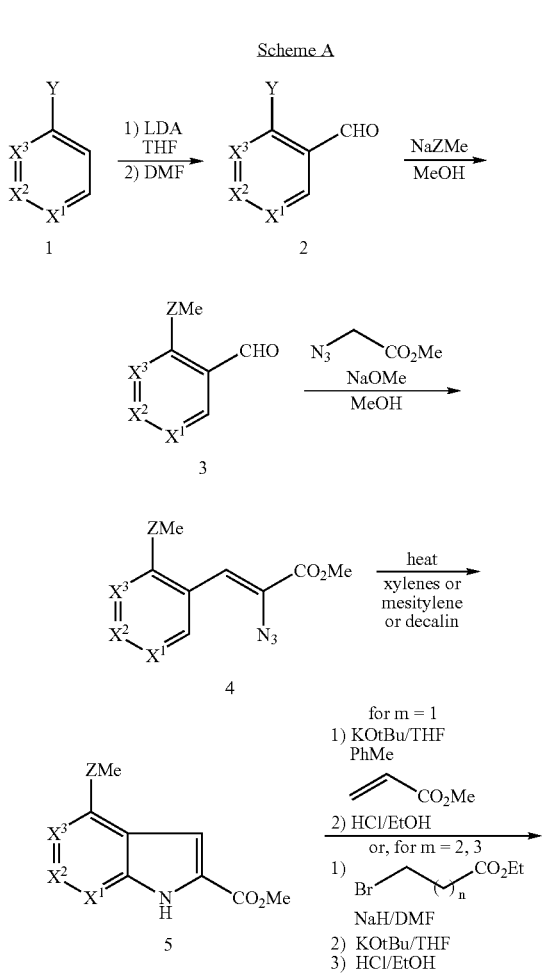

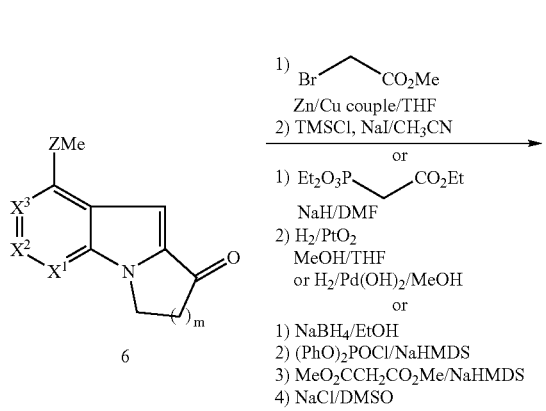

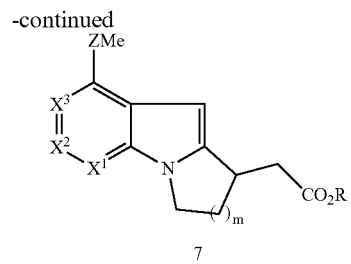

m = 1, 2, 3
R = Me, Et
Y = Cl, Br
Z = O or S

Method B

Friedel-Crafts reaction of 7 with a suitable acid chloride in 1,2-dichloroethane gives the corresponding ketone 8. Subsequent cleavage of the ester is effected with sodium hydroxide to give the acid 9. To prepare the thioether 11, a suitable disulfide is treated with $SO_2Cl_2$ in 1,2-dichloroethane to give the corresponding sulfenyl chloride, which is then allowed to react with 7 to give the thioether ester 10. Hydrolysis of 10 using aqueous sodium hydroxide provides the acid 11.

Scheme B

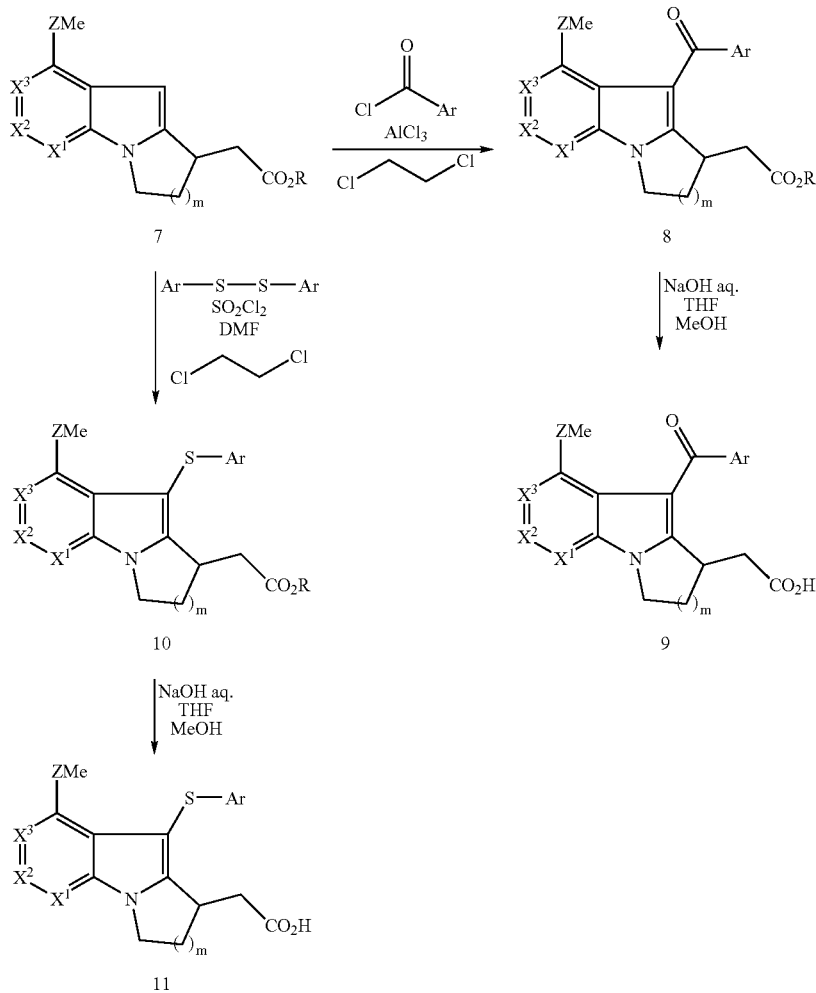

m = 1, 2, 3
Z = O or S
R = Me, Et

Method C

The thioether compound 8a can be oxidized with $Na_2WO_4$/$H_2O_2$ to afford the corresponding sulfone ester, which upon hydrolysis provides the sulfone acid 12. Compound 7a can be similarly oxidized, and the resulting sulfone 13 can be elaborated to the thioether 14 according to procedures described in Scheme B.

Emmonds reaction followed by palladium mediated coupling with 2-bromopropene and finally hydrogenation of the two olefins gives 16, which is elaborated into compound 17 as described in Scheme B. The isopropyl group can also be introduced earlier in the synthesis. The compound 2a can be converted to the azaindole ester as shown in Method A for the preparation of 5. The isopropyl is then introduced as described using palladium mediated coupling with 2-bromopropene.

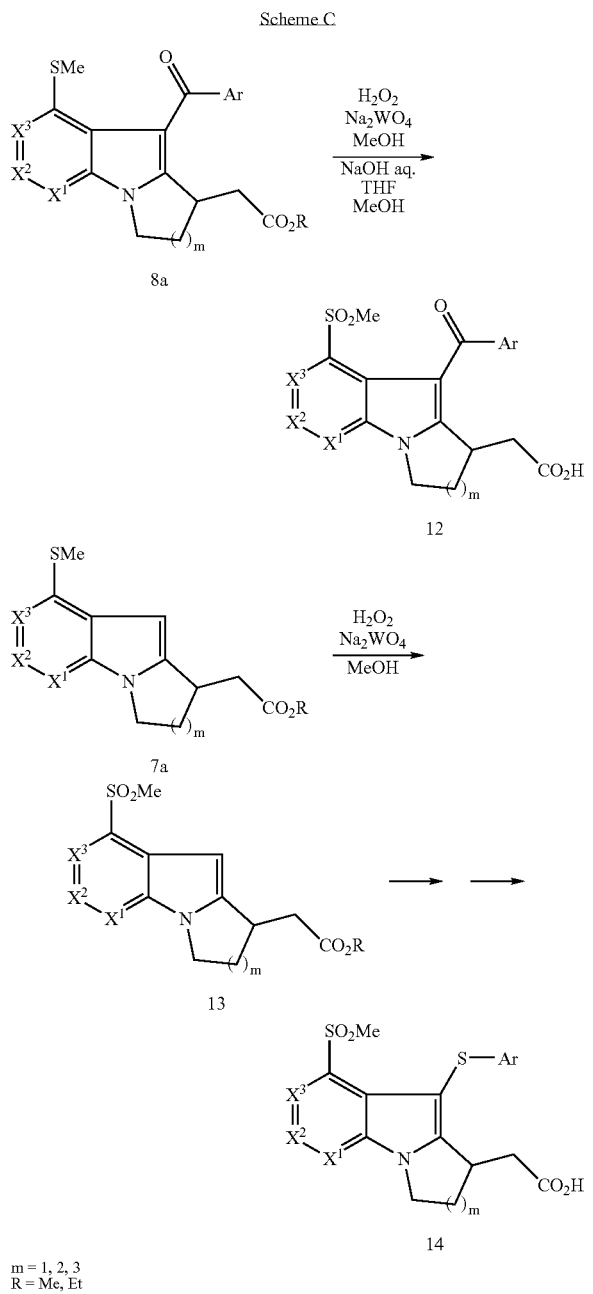

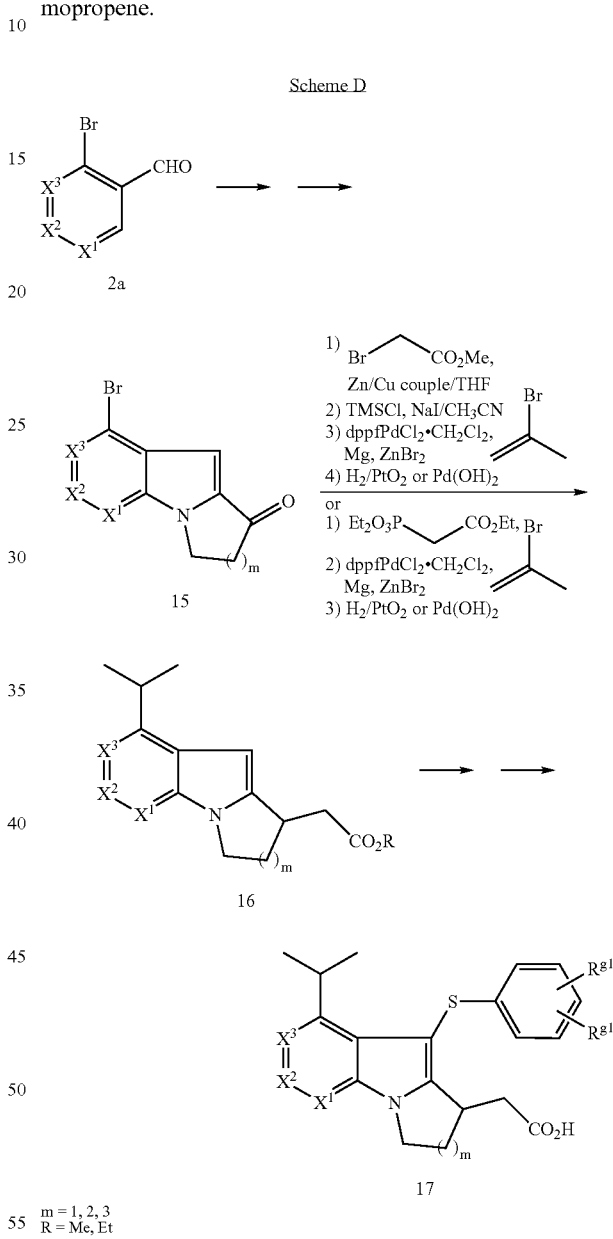

Method D

Bromopyridine aldehyde 2a is elaborated into compound 15 using the reaction steps described in Method A. Introduction of the ester and isopropyl moieties is as follows. Reformatsky reaction followed by deoxygenation with TMSCl/NaI, then palladium mediated coupling with 2-bromopropene followed by hydrogenation gives 16. Alternatively, Horner- Method E Azaindole 18 can be prepared according to the procedure in J. Heterocyclic Chem. 359 (1992). Treatment of 18 with base, followed by $CO_2$ and diazomethane gives ester 19, which is then further functionalized by chemistry described in Methods A and B to give acid 23. Alternatively, condensation of 2-pyridinecarboxaldehyde with methylazidoacetate provides azido olefin 25 which is cyclized under thermal conditions to give ester 19 which is carried on to acid 23.

Scheme E

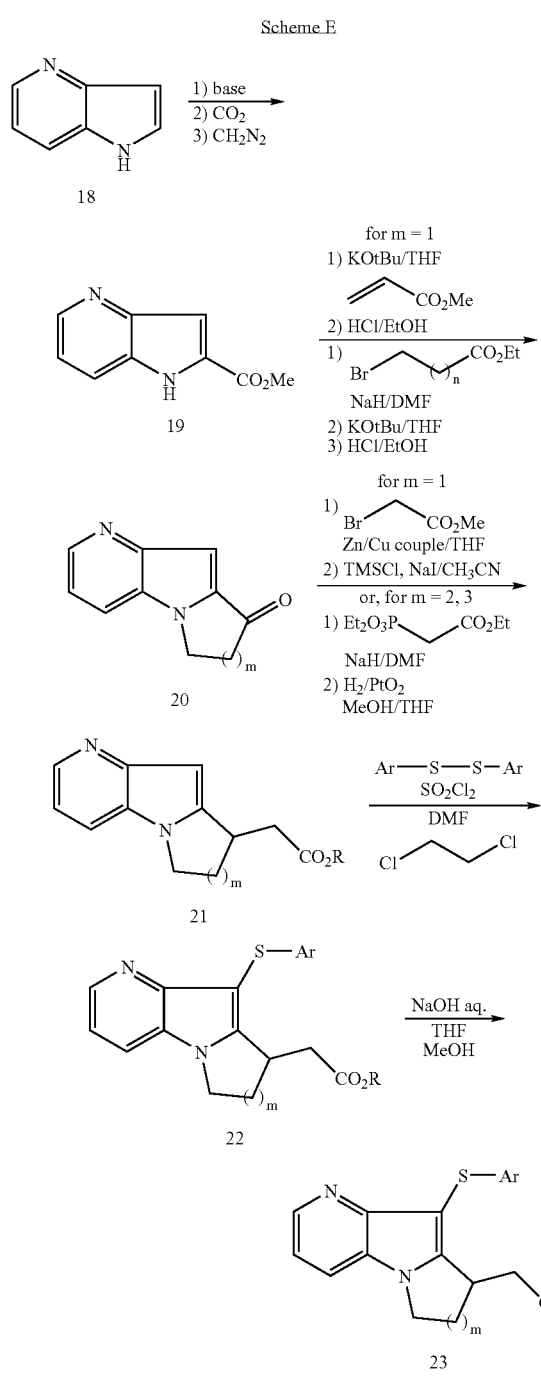

m = 1, 2, 3
R = Me, Et alternatively:

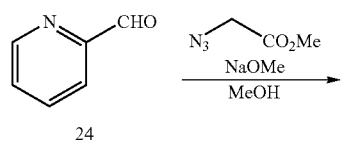

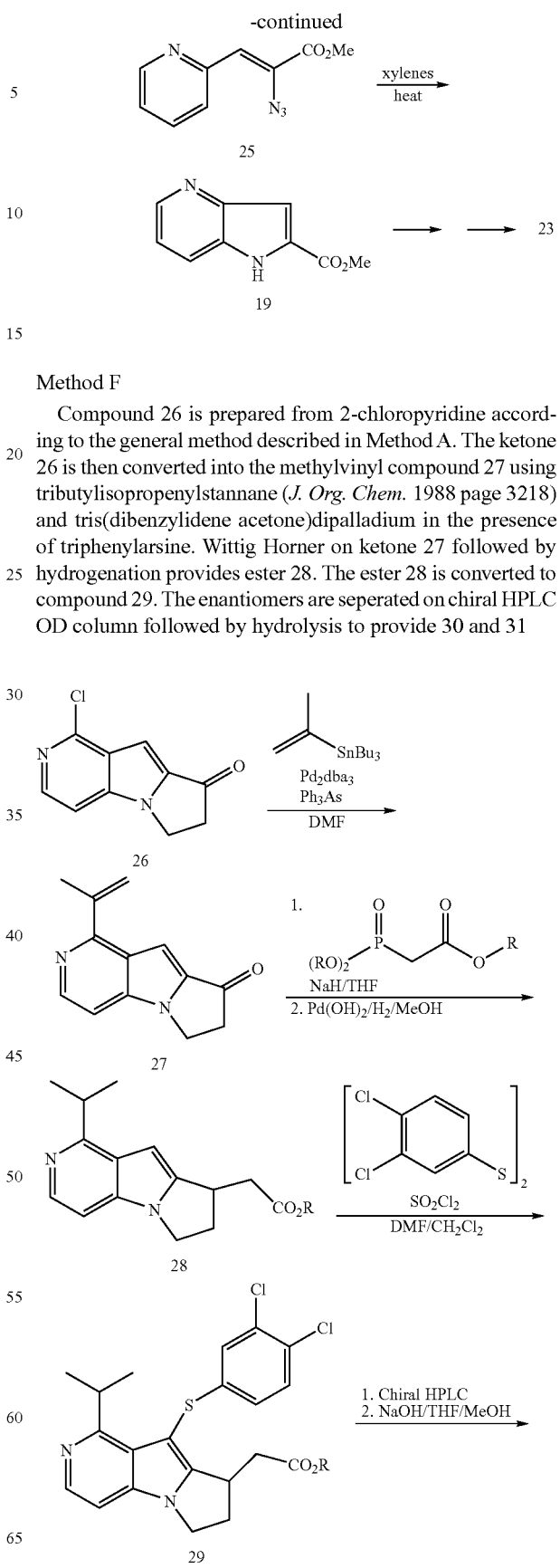

Method F

Compound 26 is prepared from 2-chloropyridine according to the general method described in Method A. The ketone 26 is then converted into the methylvinyl compound 27 using tributylisopropenylstannane (*J. Org. Chem.* 1988 page 3218) and tris(dibenzylidene acetone)dipalladium in the presence of triphenylarsine. Wittig Horner on ketone 27 followed by hydrogenation provides ester 28. The ester 28 is converted to compound 29. The enantiomers are seperated on chiral HPLC OD column followed by hydrolysis to provide 30 and 31

-continued

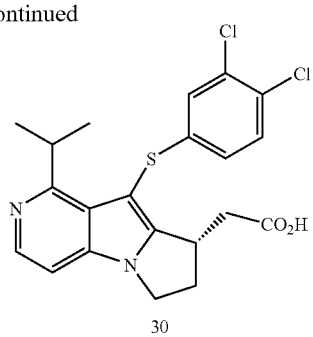

30

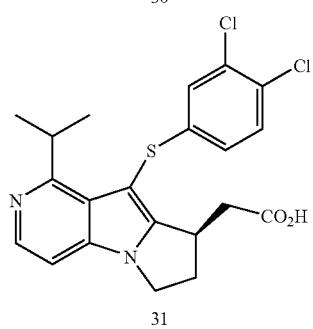

31

Assays for Determining Biological Activity

Compounds of formula I can be tested using the following assays to determine their prostanoid antagonist or agonist activity in vitro and in vivo and their selectivity. The prostaglandin receptor activities demonstrated are DP, $EP_1$, $EP_2$, $EP_3$, $EP_4$, FP, IP and TP.

Stable Expression of Prostanoid Receptors in the Human Embryonic Kidney (HEK) 293(ebna) Cell Line Prostanoid receptor cDNAs corresponding to full length coding sequences are subcloned into the appropriate sites of mammalian expression vectors and transfected into HEK 293 (ebna) cells. HEK 293(ebna) cells expressing the individual cDNAs are grown under selection and individual colonies are isolated after 2-3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 µM of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves for determination of ligand affinity.

Prostanoid Receptor Agonist and Antagonist Assays

Whole cell second messenger assays measuring stimulation ($EP_2$, $EP_4$, DP and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 µM RO-20-1724 (phosphodiesterase type IV inhibitor, available from Biomol) and, in the case of the $EP_3$ inhibition assay only, 15 µM forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both $K_B$ and slope values are calculated.

Prevention of PGD2 or Allergen Induced Nasal Congestion in Allergic Sheep

Animal preparation: Healthy adult sheeps (18-50 kg) are used. These animals are selected on the basis of a natural positive skin reaction to an intradermal injection of Ascaris suum extract.

Measurements of nasal congestion: The experiment is performed on conscious animals. They are restrained in a cart in a prone position with their heads immobilized. Nasal airway resistance (NAR) is measured using a modified mask rhinometry technique. A topical anaesthesia (2% lidocaine) is applied to the nasal passage for the insertion of a nasotracheal tube. The maximal end of the tube is connected to a pneumotachograph and a flow and pressure signal is recorded on an oscilloscope linked to a computer for on-line calculation of NAR. Nasal provocation is performed by the administration of an aerosolized solution (10 puffs/nostril). Changes in the NAR congestion are recorded prior to and for 60-120 minutes post-challenge.

Prevention of PGD2 and Allergen Induced Nasal Obstruction in Cynomolgus Monkey

Animal preparation: Healthy adult male cynomologus monkeys (4-10 kg) are used. These animals are selected on the basis of a natural positive skin reaction to an intradermal injection of Ascaris suum extract. Before each experiment, the monkey selected for a study is fasted overnight with water provided at libitum. The next morning, the animal is sedated with ketamine (10-15 mg/kg i.m.) before being removed from its home cage. It is placed on a heated table (36° C.) and injected with a bolus dose (5-12 mg/kg i.v.) of propofol. The animal is intubated with a cuffed endotracheal tube (4-6 mm I.D.) and anaesthesia is maintained via a continuous intravenous infusion of propofol (25-30 mg/kg/h). Vital signs (heart rate, blood pressure, respiratory rate, body temperature) are monitored throughout the experiment.

Measurements of nasal congestion: A measurement of the animal respiratory resistance is taken via a pneumotachograph connected to the endotracheal tube to ensure that it is normal. An Ecovision accoustic rhinometer is used to evaluate nasal congestion. This technique gives a non-invasive 2D echogram of the inside of the nose. The nasal volume and the minimal cross-sectional area along the length of the nasal cavity are computed within 10 seconds by a laptop computer equipped with a custom software (Hood Laboratories, Mass., U.S.A.). Nasal challenge is delivered directly to the animal's nasal cavity (50 μL volume). The changes in nasal congestion are recorded prior to and for 60-120 minutes post-challenge. If nasal congestion occurs, it will translate into a reduction in the nasal volume.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either PGD2 or Ascaris suum antigen; 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of mediator or Ascaris antigen response by the test compound. For statistical analysis, paired t-test is used. (References: McFarlane, C. S. et al., Prostaglandins, 28, 173-182 (1984) and McFarlane, C. S. et al., Agents Actions, 22, 63-68 (1987).)

Prevention of Induced Bronchoconstriction in Allergic Sheep

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of Ascaris suum extract (Greer Diagnostics, Lenois, N.C.); and b) they have previously responded to inhalation challenge with Ascaris suum with both an acute bronchoconstriction and a late bronchial obstruction (W. M. Abraham et al., Am. Rev. Resp. Dis., 128, 839-44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10-15 breaths is used for the determination of $R_L$. Thoracic gas volume ($V_{tg}$) is measured in a body plethysmograph, to obtain specific pulmonary resistance ($SR_L = R_L \cdot V_{tg}$).

The following examples are provided to illustrate the invention and are not to be construed as limiting the scope of the invention in any manner. In the examples, unless otherwise stated, all the end products of the formula I were analyzed by NMR, TLC and elementary analysis or mass spectroscopy;

intermediates were analyzed by NMR and TLC;

most compounds were purified by flash chromatography on silica gel, recrystallization and/or swish (suspension in a solvent followed by filtration of the solid);

the course of reactions was followed by thin layer chromatography (TLC) and reaction times are given for illustration only;

the enantiomeric excess was measured on normal phase HPLC with a chiral column: ChiralPak AD; 250×4.6 mm.

Example 1

[5-[(4-chlorophenyl)thio]-4-(methylsulfonyl)-6,7,8,9-tetrahydropyrido[3,2-b]indolizin-6-yl]acetic acid

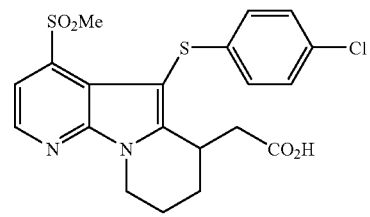

Step 1 4-chloronicotinaldehyde

The title compound was prepared as described by F. Marsais et al., J. Heterocyclic Chem., 25, 81(1988).

Step 2 4-(methylthio)nicotinaldehyde

To a solution of NaSMe (9.5 g, 135 mmol) in MeOH (250 mL) was added the 4-chloronicotinaldehyde (13.5 g, 94.4 mmol) of Step 1 in MeOH (250 mL). The reaction mixture was maintained at 60° C. for 15 min. The reaction mixture was poured over NH$_4$Cl and EtOAc. The organic phase was separated, washed with H$_2$O and dried over Na$_2$SO$_4$. The compound was then purified over silica gel with 50% EtOAc in Hexanes to provide the title compound.

Step 3 methyl (2Z)-2-azido-3-[4-(methylthio)pyridin-3-yl]prop-2-enoate

A solution of 4-(methylthio)nicotinealdehyde (4.8 g, 31 mmol) and methyl azidoacetate (9.0 g, 78 mmol) in MeOH (50 mL) was added to a solution of 25% NaOMe in MeOH (16.9 mL, 78 mmol) at −12° C. The internal temperature was monitored and maintained at −10° C. to −12° C. during the 30 min. addition. The resulting mixture was then stirred in an ice bath for several hours, followed by overnight in an ice bath in the cold room. The suspension was then poured onto a mixture of ice and $NH_4Cl$, and the slurry was filtered after 10 min. of stirring. The product was washed with cold $H_2O$ and was then dried under vacuum to give the title compound as a beige solid (7.4 g), which contained some salts. The compound is then purified over silica gel with EtOAc.

Step 4 methyl 4-(methylthio)-1H-pyrrolo[2,3-b]pyridine-2-carboxylate

A suspension of the compound of Step 3 (0.40 g, 1.6 mmol) in xylenes (16 mL) was heated slowly to 140° C. After a period of 15 min. at 140° C., the yellow solution was cooled to room temperature. Precaution must be taken due to the possibility of an exotherme due to the formation of nitrogen. The suspension was then cooled to 0° C., filtered and washed with xylene to provide the title compound.

Step 5 ethyl 4-(methylthio)-6-oxo-6,7,8,9-tetrahydropyrido[3,2-b]indolizine-7-carboxylate To a solution of the compound of Step 4 (0.35 g, 1.6 mmol) in DMF (20 mL) at 0° C. was added NaH (1.2 eq.). After a period of 5 min., were added $nBu_4NI$ (0.10 g) and ethyl 4-bromobutyrate (0.40 mL). After a period of 1 h at room temperature, the reaction mixture was poured over saturated $NH_4Cl$ and EtOAc. The organic phase was separated, washed with $H_2O$ and dried over $NaSO_4$. After evaporation the crude product was purified by flash chromatography. The bis ester was then dissolved in THF (7.0 mL) and a 1.06 M of THF solution of potassium tert-butoxide (2.2 mL) was added at 0° C. After a period of 1 h at room temperature, the reaction mixture was then poured over saturated $NH_4Cl$ and EtOAc. The organic phase was separated, dried over $Na_2SO_4$ and evaporated under reduced pressure to provide the title compound as a mixture of ethyl and methyl ester.

Step 6 4-(methylthio)-8,9-dihydropyrido[3,2-b]indolizin-6(7H)-one

To the compound of Step 5, (0.32 g) were added EtOH (8.0 mL) and concentrated HCl (2.0 mL). The resulting suspension was refluxed for 5 h. The reaction mixture was partitioned between EtOAc and $Na_2CO_3$. The organic phase was separated, evaporated to provide the title compound.

Step 7 ethyl (2E,2Z)-[4-(methylthio)-8,9-dihydropyrido[3,2-b]indolizin-6(7H)-ylidene]ethanoate To a DMF solution (12 mL) of triethyl phosphonoacetate (0.45 g, 2.17 mmol) were added 80% NaH (0.06 g, 2.00 mmol) and the compound of Step 6 (0.22 g, 1.00 mmole). After a period of 4 h at 55° C., the reaction mixture was poured over saturated $NH_4Cl$ and EtOAc. The organic phase was separated and evaporated under reduced pressure. The crude product was purified by flash chromatography to afford the title compound.

Step 8 ethyl [4-(methylthio)-6,7,8,9-tetrahydropyrido[3,2-b]indolizin-6-yl]acetate The compound of Step 7 was dissolved in MeOH—THF using heat for dissolution. To the previous cooled solution was added at room temperature $PtO_2$ and the resulting mixture was maintained for 18 h under an atmospheric pressure of hydrogen. The reaction mixture was filtered carefully over celite using $CH_2Cl_2$. The filtrate was evaporated under reduced pressure to provide the title compound. Alternatively, the compounds of Step 7 can be hydrogenated with $Pd(OH)_2$ in EtOAc at 40 PSI of $H_2$ for 18 h.

Step 9 ethyl [4-(methylsulfonyl)-6,7,8,9-tetrahydroporid[3,2-b]indolizin-6-yl]acetate To the compound of Step 8 (0.08 g, 0.27 mmol) in MeOH (3.0 mL) were added $Na_2WO_4$ (0.10 g) and 30% $H_2O_2$ (600 μL). After a period of 1 h, the reaction mixture was partitioned between $H_2O$ and EtOAc. The organic phase was washed with $H_2O$, separated and evaporated. The title compound was purified by flash chromatography.

Step 10 ethyl [5-[(4-chlorophenyl)thio]-4-(methylsulfonyl)-6,7,8,9-tetrahydropyrido[3,2-b]indolizin-6-yl]acetate To a 1,2-dichloroethane solution (2.0 mL) of 4,4'-dichlorodiphenyl disulfide (0.24 g) was added $SO_2Cl_2$ (50 μL). To the compound of Step 9 (0.05 g) in DMW (2.0 mL) was added the previous mixture (=180 μL). The reaction was followed by $^1H$ NMR and maintained at room temperature until no starting material remained. The reaction mixture was poured over saturated $NaHCO_3$ and EtOAc. The organic phase was separated, evaporated and the title compound purified by flash chromatography.

Step 11 [5-[(4-chlorophenyl)thio]-4-(methylsulfonyl)-6,7,8,9-tetrahydropyrido [3,2-b]indolizin-6-yl] acetic acid To the compound of Step 10 dissolved in a 1/1 mixture of TBF-MeOH was added 1N NaOH. After a period of 18 h at room temperature, the reaction mixture was partitioned between saturated $NH_4Cl$ and EtOAc. The organic phase was separated, dried over $Na_2SO_4$ and evaporated to provide the title compound.

$^1H$ NMR (500 MHz, acetone-$d_6$) δ 11.00 (bs, 1H), 8.60 (d, 1H), 7.80 (d, 1H), 7.20 (d, 2H), 7.00 (d, 2H), 4.65 (m, 1H), 4.20 (m, 1H), 3.75 (m, 1H), 3.35 (s, 3H), 2.80 to 2.10 (m, 6H).

Example 2

[5-[(4-chlorophenol)thio]-4-(methylthio)-6,7,8,9-tetrahydropyrido[3,2-b]indolizin-6-yl]acetic acid

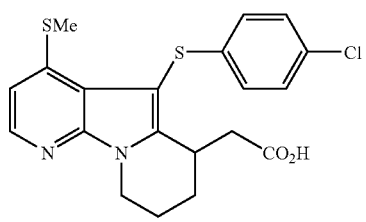

The title compound can be prepared from the compound of Example 1, Step 8 in a similar manner as described in Example 1, Step 10 and 11.

m/z 418

Example 3

[5-[(3,4-dichlorophenyl)thio]-4-(methylsulfonyl)-6,7,8,9-tetrahydropydo[3,2-b]indolizin-6-yl]acetic acid (Enantiomer A and Enantiomer B)

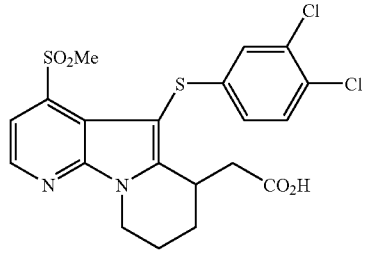

The title compound was prepared as described in Example 1 using bis(3,4-dichlorophenyl)disulfide in Step 10.

$^1$H NMR (500 MHz, acetone-$d_6$) δ 8.55 (d, 1H), 7.85 (d, 1H), 7.35 (d, 1H), 7.15 (s, 1H), 6.95 (d, 1H), 4.60 (m, 1H), 4.15 (m, 1H), 3.80 (m, 1H), 3.40 (s, 3H), 2.80 to 2.10 (m, 6H). m/z 484.

The enantiomers were separated on a Chiralecel OD column 25 cm×20 mm using 30% isopropanol, 7% ethanol, 0.2% acetic acid in hexane, flow rate 8 ml/min. Their purities were verified on a Chiralecel OD column 25 cm×4.6 mm using 35% isopropanol 0.2% acetic acid in hexane, flow rate 1.0 ml/min. More mobile enantiomer Tr=9.7 min, less mobile enantiomer Tr 11.1 min.

Example 4

[5-(4-chlorobenzoyl)-4-(methylsulfonyl)-6,7,8,9-tetrahydropyrido[3,2-b]indolizin-6-yl]acetic acid

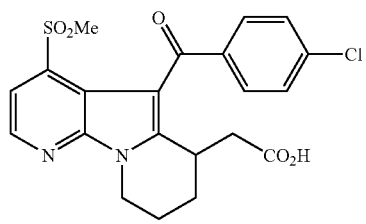

Step 1 ethyl[5-(4-chlorobenzoyl)-4-(methylthio)-6,7,8,9-tetrahydropyrido[3,2-b]indolizin-6-yl]acetate To a solution of 4-chlorobenzoyl chloride (0.30 g, 1.7 mmol) in 1,2-dichloethane (6.0 mL) was added AlCl$_3$ (0.24 g, 1.8 mmole). After a period of 5 min. a solution of ethyl [4-(methylthio)-6,7,8,9-tetrahydropyrido[3,2-b]indolizin-6-yl]acetate from Example 1 Step 8 (0.15 g, 0.47 mmole) in 1,2-dichloroethane (6.0 mL) was added to the previous mixture. After a period of 4 h, at 80° C., the reaction mixture was partitioned between EtOAc and NaHCO$_3$. The organic phase was separated, dried over Na$_2$SO$_4$ and evaporated. The title compound was purified by flash chromatography.

Step 2 ethyl[5-(4-chlorobenzoyl)-4-(methylsulfonyl)-6,7,8,9-tetrahydropyrido[3,2-b]indolizin-6-yl]acetate To a solution of ethyl[5-(4-chlorobenzoyl)-4-(methylthio)-6,7,8,9-tetrahydropyrido[3,2-b]indolizin-6yl]acetate (0.12 g, 0.27 mmole) in MeOH (5.0 mL) were added Na$_2$WO$_4$ (0.1 g) and 30% H$_2$O$_2$ (300 µL). The reaction mixture was stirred at 55° C. for 1 h. The reaction mixture was then partitioned between H$_2$O and EtOAc. The organic phase was washed with H$_2$O, dried over Na$_2$SO$_4$ and evaporated. The title compound was purified by flash chromatography.

Step 3 [5-(4-chlorobenzoyl)-4-(methylsulfonyl)-6,7,8,9-tetrahydroprdo[3,2-b]indolizin-6-yl]acetic acid Ethyl[5-(4-chlorobenzoyl)-4-(methylsulfonyl)-6,7,8,9-tetrahydropyrido[3,2-b]indolizin-6-yl]acetate was treated as described in Example 1 Step 11 to provide the title compound.

$^1$H NMR (500 MHz, acetone-$d_6$) δ 8.55 (d, 1H), 7.90 (d, 2H), 7.65 (d, 1H), 7.45 (d, 2H), 4.55 (m, 1H), 4.25 (m, 1H), 3.45 (m, 1H), 3.20 (s, 3H), 2.05 to 3.00 (m, 6H).

m/z 446

Example 5

[5-(4-bromophenyl)thio]-4-(methylsulfonyl)-6,7,8,9-tetrahydropyrdo[3,2-b]indolizin-6-yl]acetic acid

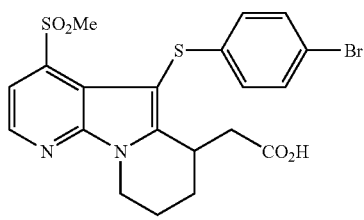

The title compound was prepared as described in Example 1 using 4,4'-dibromodiphenyl disulfide.

$^1$H NMR (500 MHz, Acetone-$d_6$) δ 8.60 (d, 1H), 7.80 (d, 1H), 7.35 (d, 2H), 7.00 (d, 2H), 4.65 (m, 1H), 4.20 (m, 1H), 3.80 (m, 1H), 3.35 (s, 3H), 2.80 to 2.10 (m, 6H).

Example 6

Method-1

[9-[(3,4-dichlorophenyl)thio]-1-(methylsulfonyl)-7,8-dihydro-6H-pyrido[3,4-b]pyrrolizin-8-yl]acetic acid

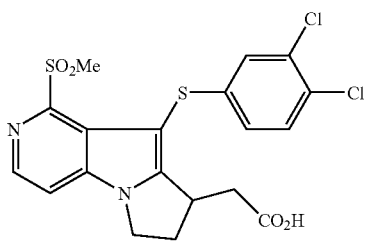

Step 1 2-(methylthio)nicotinaldehyde

The title compound was prepared from 2-bromonicotinaldehyde (A. Numata *Synthesis* 1999 p. 306) as described in Example 1 Step 2 except the solution was heated at 55° C. for 2 hr.

Step 2 methyl (2Z)-2-azido-3-[2-(methylthio)pyridin-3-yl]prop-2-enoate

The title compound was prepared as described in Example 1 Step 3.

Step 3 methyl 4-(methylthio)-1H-pyrrolo[3,2-c]pyridine-2-carboxylate

A solution of methyl (2Z)-2-azido-3-[2-(methylthio)pyridin-3-yl]prop-2-enoate (1.00 g, 4.00 mmol) in mesitylene (50 mL) was heated at 160° C. for a period of 1 h. The reaction mixture was cooled to room temperature then to 0° C., the precipitate was filtered and washed with cold mesitylene to provide the title compound.

Step 4 methyl 1-(methylthio)-8-oxo-7,8-dihydro-6H-pyrido[3,4-b]pyrrolizine-7-carboxylate To a suspension of methyl 4-(methylthio)-1H-pyrrolo[3,2-c]pyridine-2-carboxylate (0.30 g, 1.35 mmol) in TBF (3 mL)-toluene (12.0 mL) were added a 1.06 M THE solution of potassium tert-butoxide (1.42 mL/1.41 mmol) and methyl acrylate (300 μL). The resulting mixture was heated at 80° C. for 18 h. The mixture was partitioned between EtOAc and NH$_4$Cl, filtered through celite. The organic phase was separated, dried over Na$_2$SO$_4$ and filtered, to provide the title compound.

Step 5 1-(methylthio)-6,7-dihydro-8H-pyrido[3,4-b]pyrrolizin-8-one

Methyl 1-(methylthio)-8-oxo-7,8-dihydro-6H-pyrido[3,4-b]pyrrolizine-7-carboxylate was converted to the title compound as described in Example 1 Step 6.

Step 6 methyl [8-hydroxy-1-(methylthio)-7,8-dihydro-6H-pyrido[3,4-b]pyrrolizin-8-yl]acetate A mixture of 1-(methylthio)-6,7-dihydro-8H-pyrido[3,4-b]pyrrolizin-8-one (0.15 g, 0.68 mmol), methyl bromoacetate (0.34 mL), Zn—Cu (0.226 g) in THF (3.0 mL) was sonicated for 2 h. The mixture was then heated at 60° C. for 5 min. until completion of the reaction. The reaction mixture was partitioned between EtOAc and NH$_4$Cl. The organic phase was separated, dried over Na$_2$SO$_4$, filtered and evaporated under reduced pressure to provide the title compound. The compound was purified by flash chromatography.

Step 7 methyl [1-(methylthio)-7,8-dihydro-6H-pyrido[3,4-b]pyrrolizin-8-yl]acetate To NaI (0.300 g) in CH$_3$CN (3.2 mL) was added TMSCl (0.266 mL). This mixture was added to a suspension of methyl [8-hydroxy-1-(methylthio)-7,8-dihydro-6H-pyrido[3,4-b]pyrrolizin-8-yl]acetate (0.15 g, 0.515 mmol) in CH$_3$CN (1.5 mL), in a water bath. After a period of 0.5 h, the reaction mixture was partitioned between EtOAc and NaHCO$_3$. The organic phase was separated, washed with sodium thiosulphate, dried over MgSO$_4$ and evaporated. The title compound was purified by flash chromatography.

Step 8 methyl [1-(methylsulfonyl)-7,8-dihydro-6H-pyrido[3,4-b]pyrrolizin-8-yl]acetate Methyl [1-(methylthio)-7,8-dihydro-6H-pyrido[3,4-b]pyrrolizin-8-yl]acetate was converted to the title compound as described in Example 1 Step 9.

Step 9 [9-[(3,4-dichlorophenyl)thio]-1-(methylsulfonyl)-7,8-dihydro-6H-pyrido[3,4-b]pyrrolizin-8-yL] acetic acid Methyl [1-(methylsulfonyl)-7,8-dihydro-6H-pyrido[3,4-b]pyrrolizin-8-yl]acetate was converted to the title compound as described in Example 1, Steps 10 and 11, using bis (3,4-dichlorophenyl)disulfide in Step 10.

$^1$H NMR (500 MHz, acetone-d$_6$) δ 8.35 (d, 1H) 7.80 (d, 1H), 7.35 (d, 1H), 7.15 (s, 1H), 6.95 (d, 1H), 4.55 (m, 1H), 4.35 (m, 1H), 3.90 (m, 1H), 3.30 (s, 3H), 3.15 (m, 1H), 3.05 (m, 1H), 2.80 (m, 1H), 2.50 (m, 1H).

Example 6

Method-2

[9-[(3,4-dichlorophenyl)thio]-1-(methylsulfonyl)-7,8-dihydro-6H-pyrido[3,4-b]pyrrolizin-8-yl]acetic acid

Step 1 1-(methylthio)-7,8-dihydro-6H-pyrido[3,4-b]pyrrolizin-8-ol

To a suspension of 1-(methylthio)-6,7-dihydro-8H-pyrido[3,4-b]pyrrolizin-8-one from Example 6 method-1 Step 5 (0.55 g, 2.2 mmol) in EtOH (10 mL)-TH (1 mL) was added NaBH$_4$ (0.10 g, 2.6 mmol) at 0° C. After a period of 30 min. at room temperature, the reaction was quenched by the addition of acetone. The solvents were evaporated under reduced pressure and EtOAC and H$_2$O were added to the residue. The organic phase was separated, dried over MgSO$_4$ and evaporated. The title compound was washed with EtOAc/Hexane and filtered.

Step 2 dimethyl 2-[1-(methylthio)-7,8-dihydro-6H-pyrido[3,4-b]pyrrolizin-8-yl]malonate To a suspension of 1-(methylthio)-7,8-dihydro-6H-pyrido[3,4-b]pyrrolizin-8-ol (0.54 g, 2.1 mmol) in THF (10 mL) at −78° C. were added 1M NaHMDS in THF (2.35 mL, 2.4 mmol) and diphenyl chlorophosphate (0.53 mL, 2.6 mmol). After a period of 30 min. dimethyl malonate (0.73 mL, 6.4 mmol) and 1M NaHMDS in THF (6.8 mL, 6.8 mmol) were added. The reaction mixture was brought to 0° C. and then to room temperature. The mixture was then partitioned between ETOAc and NH$_4$Cl. The organic phase was dried over MgSO$_4$, filtered and evaporated. The title compound was purified by flash chromatography.

Step 3 methyl [1-(methylthio)-7,8-dihydro-6H-pyrido[3,4-b]pyrrolizin-8-yl]-acetate To a mixture of dimethyl 2-[1-(methylthio)-7,8-dihydro-6H-pyrido[3,4-b]-pyrrolizin-8-yl]malonate (0.59 g, 2.17 mmol) and DMSO (4mL) was added NaCl (0.45 g) in H$_2$O (0.45 mL). After a period of 18 h at 150° C., the reaction mixture was partitioned between ETOAc and H$_2$O. The organic phase was separated, dried over Na$_2$SO$_4$ and evaporated. The title compound was then purified by flash chromatography.

Step 4 [9-[(3,4-dichlorophenyl)thio]-1-(methylsulfonyl)-7,8-dihydro-6H-pyrido[3,4-b]pyrrolizin-8-yl] acetic acid The title compound was obtained from methyl [1-(methylthio)-7,8-dihydro-6H-pyrido-[3,4-b]pyrrolizin-8-yl]acetate as described in Example 6 Method-1 Step 8 to 9.

Example 7

[10-[(3,4-dichlorophenyl)sulfanyl]-1-(methylsulfonyl)-6,7,8,9-tetrahydropyrido[3,4-b]indolizin-9-yl]acetic acid

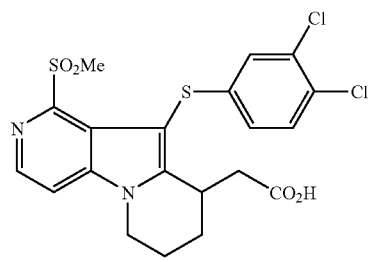

Step 1 ethyl [1-(methylsulfonyl)-6,7,8,9-tetrahydropyrido[3,4-b]indolizin-9-yl]acetate The title compound was prepared from the product of Example 6 Step 3 in the same manner as described in Example 1 Steps 5 to 9.

Step 2 [10-[(3,4-dichlorophenyl)sulfanyl]-1-(methylsulfonyl)-6,7,8,9-tetrahydropyrido[3,4-b]indolizin-9-yl]acetic acid The product of Step 1 was converted to the title compound in the same manner as Example 1, Steps 10-11, using bis(3,4-dichlorophenyl)disulfide in Step 10.

MS M+1=485

Example 8

(4-(methylsulfonyl)-5-{[4-(trifluoromethyl)phenyl]thio}-6,7,8,9-tetrahydropyrido[3,2-b]-indolizin-6-yl)acetic acid

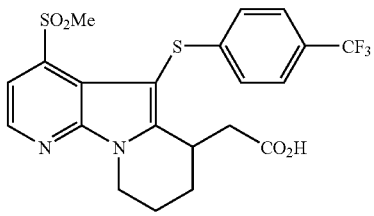

The title compound was prepared as described in Example 1 using bis[4-trifluoromethyl)phenyl]disulfide $^1$H NMR (500 MHz, acetone-$d_6$) δ 8.55 (d, 1H), 7.75 (d, 1H), 7.45 (d, 2H), 7.15 (d, 2H), 4.55 (m, 1H), 4.15 (m, 1H), 3.80 (m, 1H), 3.30 (s, 3H), 2.80 to 2.10 (m, 6H).

m/z 513 (M+1)

Example 9

[5-[(2-chloro-4-fluorophenyl)thio]-4-(methylsulfonyl)-6,7,8,9-tetrahydropyrdo[3,2-b]indolizin-6-yl]acetic acid

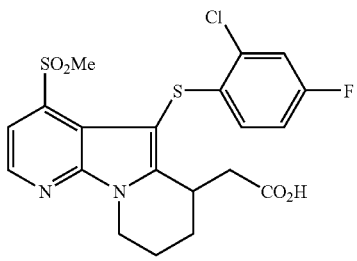

The title compound was prepared as described in Example 1 using bis(2-chloro-4-fluorophenyl)disulfide.

m/z 469 (M+1)

Example 10

[4-(methylsulfonyl)-5-(2-naphthylthio)-6,7,8,9-tetrahydropyrido[3,2-b]indolizin-6-yl]acetic acid

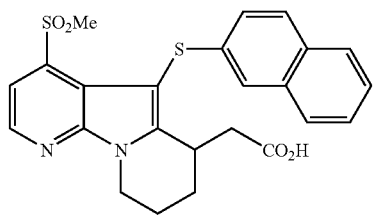

The title compound was prepared as described in Example 1 using di(2-naphthyl) disulfide.

M/z 467 (M+1)

Example 11

[5-[(2,3-dichlorophenyl)thio]-4-(methylsulfonyl)-6,7,8,9-tetrahydropyrido[3,2-b]indolizin-6-yl]acetic acid

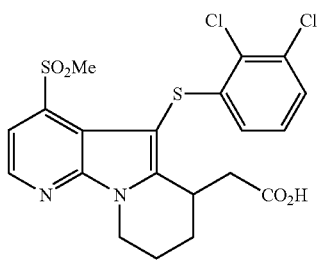

The title compound was prepared as described in Example 1 using bis(2,3-dichlorophenyl)disulfide.

$^1$H NMR (500 MHz, acetone-$d_6$) δ 8.85 (d, 1H), 7.80 (d, 1H), 7.30 (d, 1H), 7.00 (t, 1H), 6.60 (d, 1H), 4.60 (m, 1H), 4.20 (m, 1H), 3.80 (m, 1H), 3.40 (s, 3H), 2.80 to 2.10 (m, 6H).

Example 12

[5-[(4-methylphenyl)thio]-4-(methylsulfonyl)-6,7,8,
9-tetrahydropyrido[3,2-b]indolizin-6-yl]acetic acid

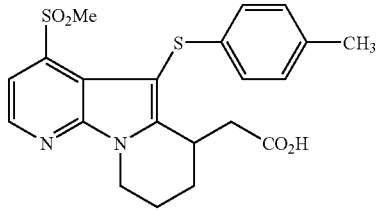

The title compound was prepared as described in Example 1 using p-tolyl disulfide.

$^1$H NMR (500 MHz, acetone-$d_6$) δ 8.55 (d, 1H), 7.80 (d, 1H), 6.95 (m, 4H), 4.60 (m, 1H), 4.15 (m, 1H), 3.80 (m, 1H), 3.35 (s, 3H), 2.80 to 2.10 (m, 6H).

Example 13

[4-(methylsulfonyl)-5-(phenylthio)-6,7,8,9-tetrahydropyrido[3,2-b]indolizin-6-yl]acetic acid

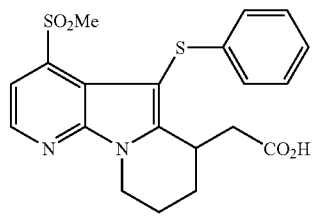

The title compound was prepared as described in Example 1 using diphenyl disulfide.

$^1$H NMR (500 MHz, acetone-$d_6$) δ 8.55 (d, 1E), 7.80 (d, 1H), 7.15 to 6.90 (m, 5H), 4.60 (m, 1H), 4.15 (m, 1H), 3.75 (m, 1H), 3.30 (s, 3H), 2.80 to 2.10 (m, 6H).

Example 14

[5-[1(2,4-dichlorophenyl)thio]-4-(methylsulfonyl)-6,
7,8,9-tetrahydropyrido[3,2-b]indolizin-6-yl]acetic acid

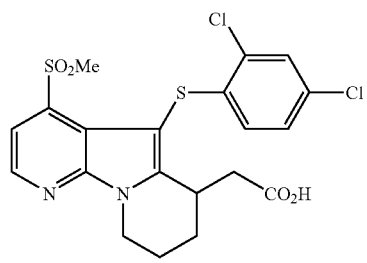

The title compound was prepared as described in Example 1 using bis(2,4-dichlorophenyl)disulfide. The disulfide was prepared from 2,4-dichlorothiophenyl using $Br_2$ in ether.

$^1$H NMR (500 MHz, acetone-$d_6$) δ 8.55 (d, 1H), 7.85 (d, 1H), 7.35 (s, 1H), 7.00 (d, 1H), 6.65 (d, 1H), 4.55 (m, 1H), 4.15 (m, 1H), 3.80 (m, 1H), 3.35 (s, 3H), 2.80 to 2.10 (m, 6H).

Example 15

[5-[(4-chlorophenyl)thio]-4-(methylsulfonyl)-6,7,8,
9-tetrahydropyrido[4,3-b]indolizin-6-yl]acetic acid

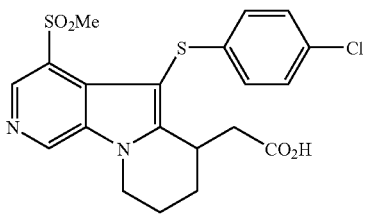

The title compound was prepared as described in Example 1 from 3-chloronicotinaldehyde (Heterocycles p. 151, 1993) except the thermal cyclization was performed by adding the azide to decalin at reflux.

$^1$H NMR (500 MHz, acetone-$d_6$) δ 9.20 (s, 1H), 8.85 (s, 1H), 7.20 (d, 2H), 7.00 (d, 2H), 4.70 (m, 1H), 4.30 (m, 1H), 3.75 (m, 1H), 3.35 (s, 3H), 2.80 to 2.10 (m, 6H).

Example 16

[9-[(4-chlorophenyl)thio]-1-(methylsulfonyl)-7,8-
dihydro-6H-pyrido[3,4-b]pyrrolizin-8-yl]acetic acid

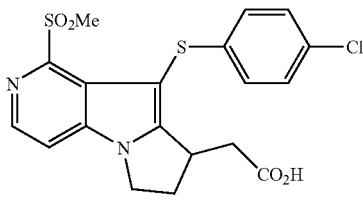

The title compound was prepared from the product of Example 6 Method 1 Step 8, as described in the procedures outlined in Example 1 Steps 10 and 11, using bis (4-chlorophenyl)disulfide in Step 10.

$^1$H NMR (500 MHz, acetone-$d_6$) δ 8.25-8.3 (m, 1H), 7.71-7.75 (m, 1H), 7.12-7.17 (m, 2H), 6.97-7.04 (m, 2H), 4.45-4.51 (m, 1H), 4.32-4.39 (m, 1H), 3.73-3.80 (m, 1H), 3.29 (s, 3H), 3.15-3.21 (m, 1H), 2.99-3.08 (m, 1H), 2.66-2.73 (m, 1H), 2.46-2.54 (m, 1H).

Example 17

{9-[(3,4-dichlorophenyl)thio]-1-isopropyl-7,8-dihydro-6H-pyrido[3,4-b]pyrrolizin-8-yl}acetic acid
(Enantiomer A and Enantiomer B)

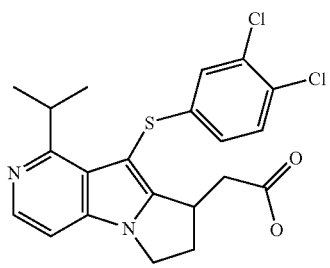

Step 1 2-chloronicotinaldehyde

To a solution of diisopropyl amine (110 mL, 780 mmol) in THF (500 mL) was added a 2.5 M hexanes solution of n-BuLi (300 mL, 750 mmol) at −40° C. After 5 min, the reaction mixture was cooled to −95° C. then DMPU (15 mL) and 2-chloropyridine (50 mL, 532 mmol) were successively added. The resulting mixture was then warmed and stirred at −78° C. for 4 h. After this time, the yellow suspension was cooled again to −95° C. before DMF (70 mL) was added. The final reaction mixture was warmed to −78° C. and stirred at that temperature for 1.5 h. The reaction mixture was poured into cold aqueous HCl (3N, 800 mL) and stirred for 5 min. Aqueous concentrated NH$_4$OH was added to adjust pH to 7.5. The aqueous layer was extracted three times with EtOAc. The combined organic layer was washed with aqueous NH$_4$Cl and brine, dried over anhydrous Na$_2$SO$_4$, filtered and concentrated. The crude material was further purified by a pad of silica gel by eluting with a gradient from 100% hexanes to 100% EtOAc and the product was crystallized in cold hexanes to yield the title compound as a pale yellow solid.

Step 2 methyl (2Z)-2-azido-3-(2-chloropyridin-3-yl)prop-2-enoate

The title compound was prepared as described in Example 1 Step 3.

Step 3 methyl 4-chloro-1H-pyrrolo[3,2-c]pyridine-2-carboxylate

The title compound was prepared in a similar manner as described in Example 6 Method-1 Step 3.

Step 4 methyl 1-chloro-8-oxo-7,8-dihydro-6H-pyrido[3,4-b]pyrrolizine-7-carboxylate To a suspension of methyl 4-chloro-1H-pyrrolo[3,2-c]pyridine-2-carboxylate (12.5 g, 59 mmol) in THF (116 mL)-toluene (460 mL) were added a 1.0 M TBF solution of potassium tert-butoxide (64 mL, 64 mmol) and methyl acrylate (55 mL, 611 mmol). The resulting mixture was heated at 100° C. for 18 h. After this time, the suspension was cooled to room temperature and it was poured into a mixture of saturated aqueous NH$_4$Cl (400 mL) and hexanes (400 mL). The solids were decanted, filtered and washed with H$_2$O and hexanes to provide the title compound.

Step 5 1-chloro-6,7-dihydro-8H-pyrido[3,4-b]pyrrolizin-8-one

The title compound was prepared in a similar manner as described in Example 1 Step 6 using isopropanol instead of ethanol and heating at 100° C. for 1 h.

Step 6 1-isopropenyl-6,7-dihydro-8H-pyrido[3,4-b]pyrrolizin-8-one

To a mixture of 1-chloro-6,7-dihydro-8H-pyrido[3,4-b]pyrrolizin-8-one (5.0 g, 24.3 mmol), tris (dibenzylideneacetone)dipalladium (0) (1.0 g, 1.09 mmol) and triphenylarsine (2.70 g, 8.82 mmol) in DMF (100 mL) was added tributylisopropenyl stannane (9.60 g, 29.00 mmol). The resulting mixture was degassed and heated at 78° C. for a period of 18 h. The solvent was evaporated under reduced pressure. CH$_2$Cl$_2$ and celite were added to the resulting mixture which was then filtered over celite. The title compound was purified by flash chromatography (50% to 100% EtOAc in Hexane).

Step 7 ethyl (2E)-(1-isopropenyl-6,7-dihydro-8H-pyrido[3,4-b]pyrrolizin-8-ylidene)ethanoate To a solution of 1-isopropenyl-6,7-dihydro-8H-pyrido[3,4-b]pyrrolizin-8-one (0.60 g, 2.8 mmol) and triethyl phosphonoacetate (1.00 g, 4.46 mmol) in THF (24 mL) at −78° C. was added 80% NaH (0.12 g, 4.00 mmol), the reaction mixture was allowed to warm to 0° C., then to room temperature. The reaction mixture was poured onto saturated NH$_4$Cl and EtOAc. The organic phase was separated, dried over Na$_2$SO$_4$ and evaporated. The title compound was purified by flash chromatography (40% EtOAc in Hexane).

Step 8 ethyl (1-isopropyl-7,8-dihydro-6H-pyrido[3,4-b]pyrrolizin-8-yl)acetate To a solution of ethyl (2E)-(1-isopropenyl-6,7-dihydro-8H-pyrido[3,4-b]-pyrrolizin-8-ylidene)ethanoate (0.40 g, 1.4 mmol) in MeOH (20 mL) was added Pd(OH)$_2$ (0.20 g). The mixture was stirred under 1 atm of H$_2$ for 3 h. The mixture was filtered over celite and evaporated to provide the title compound.

Step 9 ethyl {9-[(3,4-dichlorophenyl)thio]-1-isopropyl-7,8-dihydro-6H-pyrido[3,4-b]pyrrolizin-8-yl}acetate To a solution of bis (3,4-dichlorophenyl)disulfide (0.24 g, 0.67 mmol) in CH$_2$Cl$_2$ (5.6 mL) was added SO$_2$Cl$_2$ (0.036 mL). The resulting yellow mixture was stirred at room temperature for 1 h. This solution was added to a solution of ethyl (1-isopropyl-7,8-dihydro-6H-pyrido[3,4b]pyrrolizin-8-yL) acetate (0.15 g, 0.52 mmol) in DMF (5.6 mL) at 0° C. After 1.5 h 0° C., the reaction mixture was poured over saturated NaHCO$_3$ and EtOAc. The organic phase was separated, dried over Na$_2$SO$_4$, filtered and evaporated. The title compound was purified by flash chromatography (30% to 40% EtOAc in Hexane).

Step 10 {9-[(3,4-dichlorophenyl)thio]-1-isopropyl-7,8-dihydro-6H-pyrido[3,4-b]pyrrolizin-8-yl}acetic acid To a solution of ethyl {9-[(3,4-dichlorophenyl)thio]-1-isopropyl-7,8-dihydro-6H-pyrido[3,4-b]pyrrolizin-8-yl}acetate (0.23 g, 0.50 mmol) in THF (5 mL and MeOH (2.5 mL) was added 1.0 M NaOH (1.5 mL, 1.5 mmol). After stirring 18 h at RT, HOAc (0.25 mL) was added and the solvent was evaporated. The residue was taken up in EtOAc/H$_2$O, and the organic layer was washed with H$_2$O and brine. After drying (Na$_2$SO$_4$), the solution was filtered and evaporated. The residue was stirred with 1:1 EtOAc:hex to give, after filtration, the title compound as a white solid.

$^1$H NMR (MeOH-d$_4$) δ 1.14-1.26 (m, 6H), 2.47-2.56 (m, 1H), 2.56-2.64 (m, 1H), 2.94-3.05 (m, 2H), 3.81-3.89 (m, 1H), 4.22-4.30 (m, 1H), 4.33-4.44 (m, 2H), 6.93-6.99 (m, 1H), 7.14-7.19 (m, 1H), 7.33-7.39 (m, 1H), 7.54-7.59 (m, 1H), 8.16-8.21 (m, 1H).

The product of Step 10 was converted to its methyl ester using CH$_2$N$_2$, and the ester was subjected to HPLC separation on chiral stationary phase (chiralcel OD column 2×25 cm), eluting with 12% 2-propanol in hexane at a flow rate of 6 mL/min. Enantiomer A (less polar) has a retention time of 31.9 min and Enantiomer B (more polar) has a retention time of 35.5 min. Both A and B were hydrolyzed as in Ex. 17 Step 10 to give enantiomers A and B of the title compound.

What is claimed is:
1. A compound having the formula I

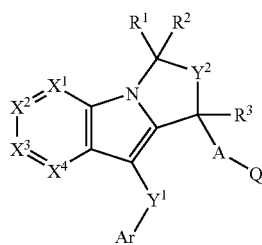

and pharmaceutically acceptable salts thereof, wherein:
A is selected from $C_{1-3}$alkyl optionally substituted with one to four halogen atoms, $O(CH_2)_{1-2}$, and $S(CH_2)_{1-2}$;
Ar is selected from phenyl, 2-, 3-, 4-chlorophenyl, 2-, 3-, 4-bromophenyl, 2-, 3-, 4-fluorophenyl, 3,4-dichlorophenyl, 2,3-dichlorophenyl, 2,4-dichlorophenyl, 2,5-dichlorophenyl, 2,6-dichlorophenyl, 3,5-dichlorophenyl, 3-chloro-4-fluorophenyl, 2-chloro-4-fluorophenyl, 4-chloro-2-fluorophenyl, 2-cyanophenyl, 4-methylphenyl, 4-isopropylphenyl, 4-trifluoromethylphenyl, biphenyl, naphthyl, 3-methoxyphenyl, 3-carboxyphenyl, 2-carboxamidophenyl, 4-methoxyphenyl, 3-phenoxyphenyl, 4-(4-pyridyl)phenyl, 4-methylsulfonylphenyl, 3-dimethylaminophenyl, 5-tetrazolyl, 1-methyl-5-tetrazolyl, 2-methyl-5-tetrazolyl, 2-benzothienyl, 2-benzofuranyl, 2-indolyl, 2-quinolinyl, 7-quinolinyl, 2-benzothiazolyl, 2-benzimidazolyl, 1-benzotriazolyl, 2-furanyl, 3-furanyl, 2-imidazolyl, 5-imidazolyl, 5-isoxazolyl, 4-isoxazolyl, 4-isothiazolyl, 1,2,4-oxadiazol-5-yl, 2-oxazolyl, 4-oxazolyl, 4-pyrazolyl, 5-pyrazolyl, 2-pyridyl, 3-pyridyl, 2-pyrazinyl, 5-pyrimidinyl, 2-pyrrolyl, 4-thiazolyl, 1,2,4-thiadiazol-3-yl, 1,2,5-thiadiazol-4-yl, 1,2,3-thiadiazol-4-yl, 1,2,5-oxadiazol-4-yl, 1,2,3-oxadiazol-4-yl, 1,2,4-triazol-5-yl, 1,2,3-triazol-4-yl, 3-thienyl, 1,2,4-triazol-5-yl, pyrrolopyridine, furo[3,2-b]pyridin-2-yl, thieno[2,3-b]pyridin-2-yl, 5(H)-2-oxo-4-furanyl, 5(H)-2-oxo-5-furanyl, (1H-4H)-5-oxo-1,2,4-triazol-3-yl, 4-oxo-2-benzopyranyl;
Q is COOH,
one of $X^1$, or $X^3$ is nitrogen and the others are independently selected from CH and C—$R^g$ and $R^g$ is selected from 1) $C_{1-6}$alkyl optionally substituted with $OR^a$, or 2) $S(O)_nC_{1-6}$alkyl;
$X^2$ is CH;
$X^4$ is CH or C—$R^g$, where $R^g$ is selected from 1) $C_{1-6}$alkyl optionally substituted with $OR^a$ or 2) $S(O)_nC_{1-6}$alkyl;
$Y^1$ is S;
$Y^2$ is selected from $(CR^dR^e)_m$ and $CR^d$=$CR^e$;
$R^1$ is H;
$R^2$ is H;
$R^3$ is H;
$R^a$ is independently selected from H and $C_{1-10}$alkyl;
$R^d$ and $R^e$ are independently H, halogen, $C_{1-6}$alkyl or halo$C_{1-6}$alkyl;
m is 1 or 2; and
n is 0, 1 or 2.
2. A compound of claim 1 wherein A-Q is $CH_2CO_2H$.

3. A compound of claim 1 wherein one of $X^1$ and $X^3$ is nitrogen and the other is CH, $X^2$ is CH, and $X^4$ is C—$S(O)_n$—$C_{1-6}$alkyl or C—$C_{1-6}$alkyl optionally substituted with $OR^a$.
4. A compound of claim 1 wherein $Y^2$ is selected from $CH_2$ and $CH_2CH_2$.
5. A compound of claim 1 represented by the formula Ia:

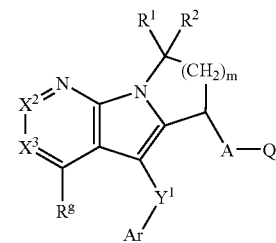

wherein $X^2$ and $X^3$ are independently CH or C—$R^g$, A, Ar, Q, $Y^1$, $R^1$, $R^2$, m and $R^g$ are as defined in claim 1.
6. A compound of claim 5 wherein $X^2$ and $X^3$ are each CH, $R^1$ and $R^2$ are each H, and A-Q is $CH_2CO_2H$.
7. A compound of claim 5 wherein $Y^1$—Ar is S-phenyl optionally substituted with 1 or 2 groups independently selected from halogen, $C_{1-6}$ alkyl and trifluoromethyl.
8. A compound of claim 1 represented by the formula Ib:

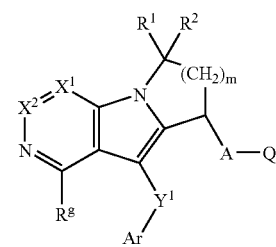

wherein $X^1$ and $X^2$ are independently CH or C—$R^g$, A, Ar, Q, $Y^1$, $R^1$, $R^2$, m and $R^g$ are as defined in claim 1.
9. A compound of claim 8 wherein $X^1$ and $X^2$ are each CH, $R^1$ and $R^2$ are each H, and A-Q is $CH_2CO_2H$.
10. A compound of claim 9 wherein $Y^1$—Ar is S-phenyl optionally substituted with 1 or 2 groups independently selected from halogen, $C_{1-6}$ alkyl and trifluoromethyl.
11. A compound of claim 1 represented by the formula Ic:

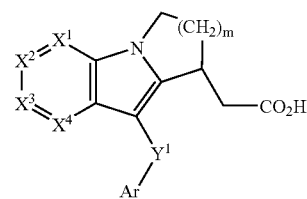

wherein one of $X^1$ and $X^3$ is N and the other is CH, $X^4$ is CH, $X^4$ is $CR^g$, m is 1 or 2, and Ar, $Y^1$ and m are as defined in claim 1.
12. A compound of claim 11 wherein Ar is phenyl optionally substituted with 1 or 2 groups independently selected from halogen, $C_{1-3}$alkyl and trifluoromethyl.

13. A compound of claim 11 wherein $X^4$ is selected from C—S(O)$_n$C$_{1-6}$alkyl and C—C$_{1-6}$alkyl optionally substituted with OR$^a$.

14. A compound of claim 11 wherein $Y^1$—Ar is S-phenyl optionally substituted with 1 or 2 groups independently selected from halogen, C$_{1-6}$alkyl and trifluoromethyl; $X^1$ and $X^2$ are each CH, $X^3$ is N, m is 1 or 2, and $X^4$ is C—SO$_2$—C$_{1-6}$alkyl or C—C$_{1-6}$alkyl.

15. A compound of claim 1 selected from:

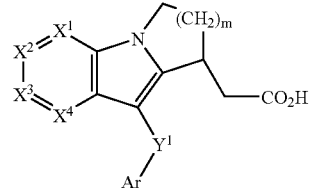

| $X^1$ | $X^2$ | $X^3$ | $X^4$ | Ar | $Y^1$ | m |
|---|---|---|---|---|---|---|
| N | CH | CH | C(SO$_2$CH$_3$) | 4-Cl—Ph | S | 2 |
| N | CH | CH | C(SCH$_3$) | 4-Cl—Ph | S | 2 |
| N | CH | CH | C(SO$_2$CH$_3$) | 3,4-diCl—Ph | S | 2 |
| N | CH | CH | C(SO$_2$CH$_3$) | 4-Br—Ph | S | 2 |
| CH | CH | N | C(SO$_2$CH$_3$) | 3,4-diCl—Ph | S | 1 |
| CH | CH | N | C(SO$_2$CH$_3$) | 3,4-diCl—Ph | S | 2 |
| N | CH | CH | C(SO$_2$CH$_3$) | 4-CF$_3$—Ph | S | 2 |
| N | CH | CH | C(SO$_2$CH$_3$) | 2-Cl-4-F—Ph | S | 2 |
| N | CH | CH | C(SO$_2$CH$_3$) | 2-naphthyl | S | 2 |
| N | CH | CH | C(SO$_2$CH$_3$) | 2,3-diCl—Ph | S | 2 |
| N | CH | CH | C(SO$_2$CH$_3$) | 4-CH$_3$—Ph | S | 2 |
| N | CH | CH | C(SO$_2$CH$_3$) | Ph | S | 2 |
| N | CH | CH | C(SO$_2$CH$_3$) | 2,4-diCl—Ph | S | 2 |
| CH | CH | N | C(SO$_2$CH$_3$) | 4-Cl—Ph | S | 2 |
| N | C(CH3) | CH | C(SO$_2$CH$_3$) | 4-Cl—Ph | S | 2 |
| N | CH | C(CH3) | C(SO$_2$CH$_3$) | 4-Cl—Ph | S | 2 |
| CH | C(CH3) | N | C(SO$_2$CH$_3$) | 4-Cl—Ph | S | 2 |
| C(CH3) | CH | N | C(SO$_2$CH$_3$) | 4-Cl—Ph | S | 2 |
| N | CH | CH | C(CH(CH$_3$)$_2$) | 4-F—Ph | S | 2 |
| N | CH | CH | C(CH(CH$_3$)$_2$) | 4-Cl—Ph | S | 2 |
| N | CH | CH | C(CH(CH$_3$)$_2$) | 2,4-diCl—Ph | S | 2 |
| N | CH | CH | C(CH(CH$_3$)$_2$) | 4-Br—Ph | S | 2 |
| N | CH | CH | C(CH(CH$_3$)$_2$) | 2-Cl-4-F—Ph | S | 2 |
| N | CH | CH | C(CH(CH$_3$)$_2$) | 3,4-diCl—Ph | S | 2 |
| CH | CH | N | C(CH(CH$_3$)$_2$) | 4-F—Ph | S | 2 |
| CH | CH | N | C(CH(CH$_3$)$_2$) | 4-Cl—Ph | S | 2 |
| CH | CH | N | C(CH(CH$_3$)$_2$) | 2,4-diCl—Ph | S | 2 |
| CH | CH | N | C(CH(CH$_3$)$_2$) | 4-Br—Ph | S | 2 |
| CH | CH | N | C(CH(CH$_3$)$_2$) | 2-Cl4-F—Ph | S | 2 |
| CH | CH | N | C(CH(CH$_3$)$_2$) | 3,4-diCl—Ph | S | 2 |
| CH | CH | N | C(CH(CH$_3$)$_2$) | 4-F—Ph | S | 1 |
| CH | CH | N | C(CH(CH$_3$)$_2$) | 4-Cl—Ph | S | 1 |
| CH | CH | N | C(CH(CH$_3$)$_2$) | 2,4-diCl—Ph | S | 1 |
| CH | CH | N | C(CH(CH$_3$)$_2$) | 4-Br—Ph | S | 1 |
| CH | CH | N | C(CH(CH$_3$)$_2$) | 2-Cl-4-F—Ph | S | 1 |
| CH | CH | N | C(CH(CH$_3$)$_2$) | 3,4-diCl—Ph | S | 1 |
| N | CH | CH | C(CH(OCH$_3$)(CH$_2$CH$_3$)) | 4-Cl—Ph | S | 2 |
| N | CH | CH | C(CH(OCH$_3$)(CH$_2$CH$_3$)) | 4-Cl—Ph | S | 1 |
| CH | CH | N | C(CH(OCH$_3$)(CH$_2$CH$_3$)) | 4-Cl—Ph | S | 2 |
| CH | CH | N | C(CH(OCH$_3$)(CH$_2$CH$_3$)) | 4-Cl—Ph | S | 1 |
| N | CH | CH | C(C(CH$_3$)$_3$) | 4-Cl—Ph | S | 2 |
| N | CH | CH | C(C(CH$_3$)$_3$) | 3,4-diCl—Ph | S | 2 |
| N | CH | CH | C(C(CH$_3$)$_3$) | 4-Br—Ph | S | 2 |
| N | CH | CH | C(C(CH$_3$)$_3$) | 4-CF$_3$—Ph | S | 2 |
| N | CH | CH | C(C(CH$_3$)$_3$) | 2-Cl-4-F—Ph | S | 2 |
| N | CH | CH | C(C(CH$_3$)$_3$) | 2-naphthyl | S | 2 |
| N | CH | CH | C(C(CH$_3$)$_3$) | 2,3-diCl—Ph | S | 2 |
| N | CH | CH | C(C(CH$_3$)$_3$) | 4-CH$_3$—Ph | S | 2 |
| N | CH | CH | C(C(CH$_3$)$_3$) | Ph | S | 2 |
| N | CH | CH | C(C(CH$_3$)$_3$) | 2,4-diCl—Ph | S | 2 |

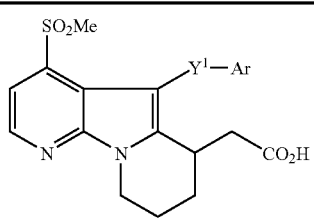

| Ar | $Y^1$ |
|---|---|
| 5-tetrazolyl | S |
| 2-pyrroly | S |
| 1,2,4-triazoly-3-yl | S |
| 1,2,3-triazol-4-yl | S |
| 5-imidazolyl | S |
| 4-pyrazolyl | S |
| 5-pyrazolyl | S |
| (1H,4H)-5-oxo-1,2,4-triazol-3-yl | S |
| 4-isothiazolyl | S |
| 1,2,5-thiadiazol-5-yl | S |
| 1,2,5-oxadiazol-5-yl | S |
| 3-furanyl | S |
| 1,2,3-thiadiazol-4-yl | S |
| 1,2,3-oxadiazol-4-yl | S |
| 4-isoxazolyl | S |
| 3-thienyl | S |
| 4-oxazolyl | S |
| 4-thiazolyl | S |
| (5H)-2-oxo-5-furanyl | S |
| (5H)-2-oxo-4-furanyl | S |
| 1,2,4-oxadiazol-5-yl | S |
| 3-pyridyl | S |
| 2-pyrazinyl | S |
| 5-pyrimidinyl | S |
| 2-indolyl | S |
| 2-benzothienyl | S |
| 2-benzofuranyl | S |
| 4-oxo-benzopyran-2-yl | S |
| 2-quinolinyl | S |
| 2-benzimidazolyl | S |
| 2-benzoxazolyl | S |
| 2-benzothiazolyl | S |
| 1-benzotriazolyl | CH$_2$S |
| thieno[2,3-b]pyridin-2-yl | S. |

16. A pharmaceutical composition comprising a compound of claim 1 and a pharmaceutically acceptable carrier.

\* \* \* \* \*